United States Patent [19]
Baylin et al.

[11] Patent Number: 5,922,590
[45] Date of Patent: Jul. 13, 1999

[54] TUMOR SUPPRESSOR GENE, HIC-1

[75] Inventors: Stephen B. Baylin, Baltimore; Michele Makos Wales, Rockville, both of Md.

[73] Assignee: The Johns Hopkins University School of Medicine, Baltimore, Md.

[21] Appl. No.: 08/452,427

[22] Filed: May 25, 1995

Related U.S. Application Data

[62] Division of application No. 08/340,203, Nov. 15, 1994.

[51] Int. Cl.[6] .............................. C12N 15/12; C12N 1/15; C12N 1/21; C12N 5/10
[52] U.S. Cl. .................................. 435/252.3; 435/254.11; 435/320.1; 435/325; 536/23.5
[58] Field of Search ................................ 435/243, 252.3, 435/254.11, 320.1, 325; 536/23.5

[56] References Cited

PUBLICATIONS

Benn et al., Primary structure and expression of a chicken cDNA encoding a protein with zinc–finger motifs. Gene. vol. 106, No. 2, pp. 207–212, 1991

Bowie et al., Deciphering the message in protein sequences: tolerance to amino acid substitutions. Science. vol. 247, pp. 1306–1310, Mar. 16, 1990.

Crosby et al. The early response gene NGFI–C encodes a zinc finger transcriptional activator and is a member of the GCGGGGGCG (GSG) element–binding protein family. Molecular and Cellular Biology. vol. 11, pp. 3835–3841, 1991.

Daniel et al. Mapping of linear antigenic sites on the S glycoprotein of neurotropic murine coronavirus with synthetic peptides: a combination of nine prediction algorithms fails to identify relevant epitopes Virology. vol. 202, No. 2, pp. 540–54, Aug. 1, 1994.

Hillier et al. yf24b08.s1 Homo sapiens cDNA clone 127767 3'. EST–STS database Accession No. R08606, Apr. 5, 1995.

Liu et al. Novel zinc finger proteins that interact with the mouse gamma F–crystallin promoter and are expressed in the sclerotome during early somitogenesis. Developmental Biology. vol. 165, No. 1, pp. 165–177, 1994.

Sambrook et al. Molecular Cloning: A Laboratory Manual. 2d Ed. CSHL Press, Cold Spring Harbor, NY. Chapters 9 and 11, 1989.

Sommer et al. Evolutionary conservation pattern of zinc–finger domains of *Drosophila* segamentation genes. Proceedings of the National Academy of Sciences, USA. vol. 89, pp.10782–10786, 1992.

Baylin, et al., *Abnormal Patterns of DNA Methylation in Human Neoplasia: Potential Consequences for Tumor Progression*, Cancer Cells, 3(10):383, 1991.

Kumagai, et al., *Rapid, high–level expression of biologically active α—trichosanthin in transfected plants by an RNA viral vector*, Proc. Natl. Acad. Sci. USA, 90:427, 1993.

Pieretti, et al., *Hypermethylation at a Chromosome 17 "Hot Spot" Is a Common Event in Ovarian Cancer*, Human Pathology, 26(4) :398, 1995.

Wales, et al., *p53 activates expression of HIC–1, a new candidate tumor suppressor gene on 17p13.3*, Nature Medicine, 1(6) :570, 1995.

Jones and Buckley, *The Role of DNA Methylation in Cancer*, Advances in Cancer Research, 54:1, 1990.

*Primary Examiner*—Stephen Walsh
*Assistant Examiner*—Brian Lathrop
*Attorney, Agent, or Firm*—Fish & Richardson, P.C.

[57] ABSTRACT

Polynucleotide and polypeptide sequences encoding a novel tumor suppressor, HIC-1, are provided. Also included is a method for detecting a cell proliferative disorder associated with HIC-1. HIC-1 is a marker which can be used diagnostically, prognostically and therapeutically over the course of such disorders.

5 Claims, 9 Drawing Sheets

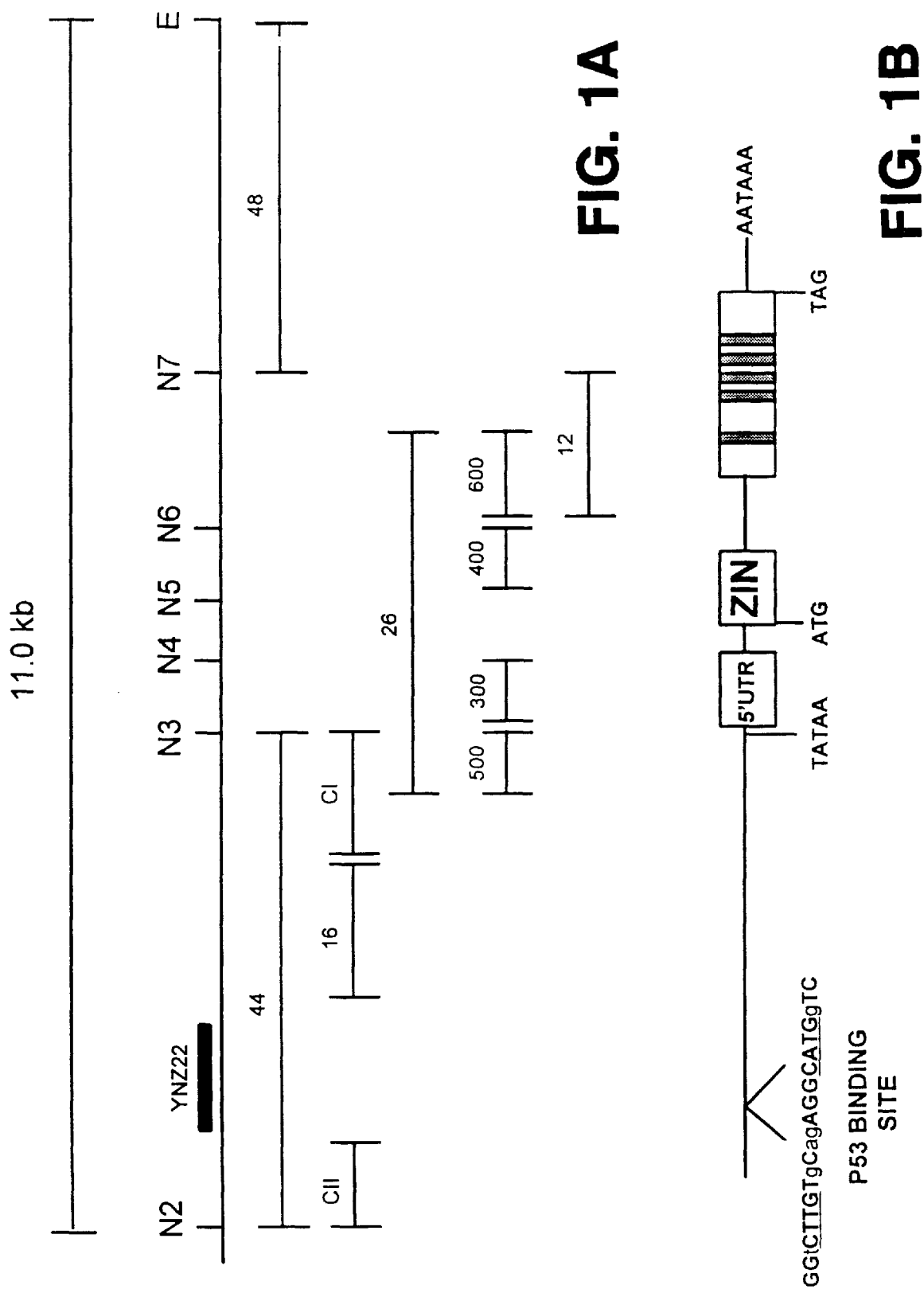

```
CCCGGCCCGC CGGGACCGCA GGTAACGGGC CGCGGGGCCC CGCGGGCCAG GAGGGGAACG    60
GGGTCGGGCG GGCGAGCAGC GGGCAGGGGA GCTCAGGGCT CGGCTCCGGG CTCTGCCGCC   120
GGATTTGGGG GCCGCGAGGA AGAGCTGCGA GCCGAGGGCC TGGGGCCGGC GCACTCCTCC   180
CGCCCTGTCT GCAGTTGGAA AACTTTTCCC CAAGTTTGGG GCGGCGGAGT TCCGGGGGAG   240
AAGGGGCCGG GGGAGCCGCG GAGGGAGGCG CCGGGCCCGC GCGTGTAGGG CCCAGGCCGA   300
GGCCGGGACG CGGGTGGGGC GCAGGCCCGG GTCAGGGCCG CAGCCGGCTG TGCGCCGTGC   360
CCGCCCGGGG CGCTGCCCCC TCCCTCCCCT GGGAGCTGCG TGGCTCCCCC CTCCCCCCCA   420
CCTGCTTCCT GCCTCAGCCT CCTGCCCCGA TATAACGCCC TCCCCGCGCC GGGCCCGGCC   480
TTCGCGCTCT GCCCGCCACG GCAGCCGCTG CCTCCGCTCC CCGCGCGGCC GCCGCCCGGG   540
CCCCGACCGA GGGTTGACAG CCCCCGGCCA GGGCGGCCGC AGGGCGGGCA CCGCGCTCCC   600
CTCCTCCGTA TCACTTCCCC CAACTGGGGC AACTTCTCCC GAGGCGGGAG GCGCTGGTTC   660
CTCGGCTCCC TTTCTCCCTA CTTGGGTAAA GTTCTCCGCC CTGAATGACT TTTCCTGAAG   720
CGGACATTTT ACTTAAATCG GGTAACTGTC TCCAAAAGGG TCACTGCGCC TGAACAGTTT   780
TCTTCTCGGA AGCCCCAGCA CCCAGCCAGG TGCCCTGGGG CGTGCAGGCC GCCCTGGCCT   840
CCCCTCCACC GGCGGCCGCT CACCTCCTGC TCCTTCTCCT GGTCCGGGCG GGCCGGCCTG   900
GGCTCCCACT CCAGAGGGCA GCTGGTCCTT CGCCGGTGCC CAGGCCGCAG GGCTGATGCC   960
CCCGCTCAGC TGAGGGAAGG GGAAGTGGAG GGGAGAAGTG CCGGGCTGGG GCCAGGCGGC  1020
CAGGGCGCCG CACGGCTCTC ACCCGGCCGG TGTGTGTCCC CGCAGGAGAG TGTGCTGGGC  1080
AGACG                                                             1127

ATG CTG GAC ACG ATG GAG GCG CCC GGC CAC TCC AGG CAG CTG
Met Leu Asp Thr Met Glu Ala Pro Gly His Ser Arg Gln Leu
 1               5                   10

CTG CTG CAG CTC AAC AAC CAG CGC ACC AAG GGC TTC TTG TGC GAC GTG   1175
Leu Leu Gln Leu Asn Asn Gln Arg Thr Lys Gly Phe Leu Cys Asp Val
15              20                  25                  30

ATC ATC GTG GTG CAG AAC GCC CTC TTC CGC GCG CAC AAG AAC GTG CTG   1223
Ile Ile Val Val Gln Asn Ala Leu Phe Arg Ala His Lys Asn Val Leu
                35                  40                  45

GCG GCC AGC AGC GCC TAC CTC AAG TCC CTG GTG GTG CAT GAC AAC CTG   1271
Ala Ala Ser Ser Ala Tyr Leu Lys Ser Leu Val Val His Asp Asn Leu
            50                  55                  60

CTC AAC CTG GAC CAT GAC ATG GTG AGC CCG GCC GTG TTC CGC CTG GTG   1319
Leu Asn Leu Asp His Asp Met Val Ser Pro Ala Val Phe Arg Leu Val
        65                  70                  75

CTG GAC TTC ATC TAC ACC GGC CGC CTG GCT GAC GGC GCA GAG GCG GCT   1367
Leu Asp Phe Ile Tyr Thr Gly Arg Leu Ala Asp Gly Ala Glu Ala Ala
    80                  85                  90

GCG GCC GCG GCC GTG GCC CCG GGG GCT GAG CCG AGC CTG GGC GCC GTG   1415
Ala Ala Ala Ala Val Ala Pro Gly Ala Glu Pro Ser Leu Gly Ala Val
95                  100                 105                 110

CTG GCC GCC GCC AGC TAC CTG CAG ATC CCC GAC CTC GTG GCG CTG TGC   1463
Leu Ala Ala Ala Ser Tyr Leu Gln Ile Pro Asp Leu Val Ala Leu Cys
                115                 120                 125

AAG AAA CGC CTC AAG CGC CAC GGC AAG TAC TGC CAC CTG CGG GGC GGC   1511
Lys Lys Arg Leu Lys Arg His Gly Lys Tyr Cys His Leu Arg Gly Gly
            130                 135                 140

GGC GGC GGC GGC GGC TAC GCG CCC TAT GCT ATG GCG ACG AGC TGG        1559
Gly Gly Gly Gly Gly Tyr Ala Pro Tyr Ala Met Ala Thr Ser Trp
        145                 150                 155

GCC GGG AGC GCG GCT CCC CCA GCG AGC GCT GCG AAG AGC GTG GTG GGG   1607
Ala Gly Ser Ala Ala Pro Pro Ala Ser Ala Ala Lys Ser Val Val Gly
160                 165                 170
```

FIG. 1C

```
ACG CGG CCG TCT CGC CCG GGG GGC CCC CGC TCG GCC TGG CGC CGC CGC        1655
Thr Arg Pro Ser Arg Pro Gly Gly Pro Arg Ser Ala Trp Arg Arg Arg
175             180              185             190

CGC GCT ACC CTG GCA GCC TGG ACG GGC CCG GCG CGG GCG GCG ACG GCG        1703
Arg Ala Thr Leu Ala Ala Trp Thr Gly Pro Ala Arg Ala Ala Thr Ala
            195             200             205

ACG ACT ACA AGA GCA GCA GCG AGG AGA CCG GTA GCA GCG AGG ACC CCA        1751
Thr Thr Thr Arg Ala Ala Ala Arg Arg Pro Val Ala Ala Arg Thr Pro
        210             215             220

GCA CCG CCT GGC GGC CAC CTC GAG GGC TAC CCA TGC CCG CAC CTG GCC        1799
Ala Pro Pro Gly Gly His Leu Glu Gly Tyr Pro Cys Pro His Leu Ala
            225             230             235

TAT GGC GAG CCC GAG AGC TTC GGT GAC AAC CTG TAC GTG TGC ATT CCG        1847
Tyr Gly Glu Pro Glu Ser Phe Gly Asp Asn Leu Tyr Val Cys Ile Pro
        240             245             250

TGC GGC AAG GGC TTC CCC AGC TCT GAG CAG CTG AAC GCG CAC GTG GAG        1895
Cys Gly Lys Gly Phe Pro Ser Ser Glu Gln Leu Asn Ala His Val Glu
255             260             265             270

GCT CAC GTG GAG GAG GAG GAA GCG CTG TAC GGC AGG GCC GAG GCG GCC        1943
Ala His Val Glu Glu Glu Glu Ala Leu Tyr Gly Arg Ala Glu Ala Ala
            275             280             285

GAA GTG GCC GCT GGG GCC GCC GGC CTA GGG CCC CCT TTT GGA GGC GGC        1991
Glu Val Ala Ala Gly Ala Ala Gly Leu Gly Pro Pro Phe Gly Gly Gly
        290             295             300

GGG GAC AAG GTC GCC GGG GCT CCG GGT GGC CTG GGA GAG CTG CTG CGG        2039
Gly Asp Lys Val Ala Gly Ala Pro Gly Gly Leu Gly Glu Leu Leu Arg
        305             310             315

CCC TAC CGC TGC GGC TCG TGC GAC AAG AGC TAC AAG GAC CCG GCC ACG        2087
Pro Tyr Arg Cys Gly Ser Cys Asp Lys Ser Tyr Lys Asp Pro Ala Thr
        320             325             330

CTG CGG CAG CAC GAG AAG ACG CAC TGG CTG ACC CGG CCC TAC CCA TGC        2135
Leu Arg Gln His Glu Lys Thr His Trp Leu Thr Arg Pro Tyr Pro Cys
335             340             345             350

ACC ATC TGC GGG AAG AAG TTC ACG CAG CGT GGG ACC ATG ACG CGC CAC        2183
Thr Ile Cys Gly Lys Lys Phe Thr Gln Arg Gly Thr Met Thr Arg His
            355             360             365

ATG CGC AGC CAC CTG GGC CTC AAG CCC TTC GCG TGC GAC GCG TGC GGC        2231
Met Arg Ser His Leu Gly Leu Lys Pro Phe Ala Cys Asp Ala Cys Gly
            370             375             380

ATG CGG TTC ACG CGC CAG TAC CGC CTC ACC CGG ACG CAC ATG CGC ATC        2279
Met Arg Phe Thr Arg Gln Tyr Arg Leu Thr Arg Thr His Met Arg Ile
        385             390             395

CAC CCT CGC GGC GAG AAG CCC TAC GAG TGC CAG GTG TGC GGC GGC AAG        2327
His Pro Arg Gly Glu Lys Pro Tyr Glu Cys Gln Val Cys Gly Gly Lys
400             405             410

TTC GCA CAG CAA CGC AAC CTC ATC AGC CAC ATG AAG ATG CAC GCC GTG        2375
Phe Ala Gln Gln Arg Asn Leu Ile Ser His Met Lys Met His Ala Val
415             420             425             430
```

FIG. 1D

| | |
|---|---:|
| GGG GGC GCG GCG GCG CGG CCG GGG CGC TGG CGG GCT TGG GGG GGC TCC<br>Gly Gly Ala Ala Ala Arg Pro Gly Arg Trp Arg Ala Trp Gly Gly Ser<br>435                        440                    445 | 2423 |
| CCG GCG TCC CCG GCC CCG ACG GCA AGG GCA AGC TCG ACT TCC CCG AGG<br>Pro Ala Ser Pro Ala Pro Thr Ala Arg Ala Ser Ser Thr Ser Pro Arg<br>450                       455                     460 | 2471 |
| GCG TCT TTG CTG TGG CTC GCT CAC GGC CGA GCA GCT GAG CCT GAA GCA<br>Ala Ser Leu Leu Trp Leu Ala His Gly Arg Ala Ala Glu Pro Glu Ala<br>465                       470                    475 | 2519 |
| GCA GGA CAA GGC GGC CGC GAC CGA GCT GCT GGC GCA GAC CAC GCA CTT<br>Ala Gly Gln Gly Gly Arg Asp Arg Ala Ala Gly Ala Asp His Ala Leu<br>480                     485                    490 | 2567 |
| CCT GCA CGA CCC CAA GGT GGC GCT GGA GAG CCT CTA CCC GCT GGC CAA<br>Pro Ala Arg Pro Gln Gly Gly Ala Gly Glu Pro Leu Pro Ala Gly Gln<br>495                 500                   505                  510 | 2615 |
| GTT CAC GGC CGA GCT GGG CCT CAG CCC CGA CAA GGC GGC CGA GGT GCT<br>Val His Gly Arg Ala Gly Pro Gln Pro Arg Gln Gly Gly Arg Gly Ala<br>515                     520                    525 | 2663 |
| GAG CCA GGG CGC TCA CCT GGC GGC CGG GCC CGA CGG CGG ACC ATC GAC<br>Glu Pro Gly Arg Ser Pro Gly Gly Arg Ala Arg Arg Arg Thr Ile Asp<br>530                     535                    540 | 2711 |
| CGT TTC TCT CCC ACC TAGAGCGCCC CTCGCCAGCC CGCTCTGTCG CTGCTGCGCG<br>Arg Phe Ser Pro Thr<br>545 | 2766 |
| GCCCTGGCCC GCACCCCAGG GAGCGGCGGG GGCGGCGCGC AGGGCCCACT GTGCCCGGGA | 2826 |
| CAACCGCAGC GTCGCCACAG TGGCGGCTCC ACCTCTCGGC GGCCTCACCT GGCCTCACTG | 2886 |
| CTTCGTGCCT TAGCTCGGGG GTCGGGGGAG AACCCCGGGA CGGGGTGGGA TGGGGTAAGG | 2946 |
| GAAATTTATA TTTTTGATAT CAGCTTTGAC CAAAGGAGAC CCCAGGCCCC TCCCGCCTCT | 3006 |
| TCCTGTGGTT CGTCGGCCCC CTCCCCCGGC TCCGCGCTGC TCTTAGAGGG GGAGGGGTGT | 3066 |
| CACTGTCGGG GCACTCCTAG CCCTACCTCC GGCCCTTGCG ACCACACCCA TTCTCACTGT | 3126 |
| GAATCTCCCC GCTGGGTCGG AGCGTCGGGC AGAGTTGGGG AGTGGGGAGG GGACTGAGCC | 3186 |
| GGCCGGAGGC CCCCGCACCC CCGCTCCCAC CCACCCCGGG ACTGATAATG TGAAGTTCCT | 3246 |
| CATTTGCAC AAGTGGCACT AGCCCAGGGC CAACCCTTCC TTCCTCAGTC ACCAAGGGCG | 3306 |
| GGGAGTTCTG GAGTCGGAAG GCGAAGAGCC TACCACCAGG TCTCCCACTC CCGCGGTGCC | 3366 |
| CTCCCTTCCC TTCCCTGCGG CCCCGGACCA TATTTATTGC ATGCGCCCCG GCGGCCCCCC | 3426 |
| ATCCCGAGCC CAGGCTGGGC TGGGCTGGAA CGCGGTCTCT TTAGCTCCCT CCTCTTCGTT | 3486 |
| TGTATATTTC CTACCTTGTA CACAGCTCTT CCAGAGCCGC TTCCATTTTC TATACTCGAA | 3546 |
| CCAAACAGCA ATAAAGCAGT AACCAAGGAC CCGACCCCG CTGCTCTCTT CTGCCCCTGC | 3606 |
| ACAAGGACCT GGATGCTGCG CCCGCTGGGT GGAGGAGCCA GAAAGGGCCA CCCTCACACA | 3666 |
| GGTGCAGAGG CTTGGACCTG CCTCCCTCCC CAGTCCCAGA AACAGATCAG CAAGAGGTCA | 3726 |
| GGTATGTTTC ATAACTAAAA ATTTATTAAG GAAACAAAAC CAGTGCTGCA AACGGGACAG | 3786 |
| AAAGGAGAGC TGGGTCTCCC TCCCGACCAC CCAGTCATCG GCCTTCCAGC TGGGGAGAGA | 3846 |
| ATCTTAAAGG AGAGGCCGGG GACCCTGTAC TCCAAAGAGC CCAGTCTTCT GAGACTCTAG | 3906 |
| GGGACTCCTA CCCCCAAACT ACTGGCCTTG GCTCCCCTAC ACGGTACCCC ATCGCTTCTG | 3966 |
| GCATAGTCCT GGGCCTCAGG GAGGGCAGAG CTGCGCACCC ATCCTCCAGG CAGGCTGTGC | 4026 |
| AGTCAGGCCA TGGGCTCTGG GGTATCCCCC ACTGGTCCCA TTAAGATTTG CCCCTGGCTC | 4086 |
| CACCGAAAAC CCCGTCTTCC CCTAAG | 4112 |

FIG. 1E

```
D.GAGA    (14-64)    GDYGTS..VSAIQLL.CH.D.V.CTLAAGGRS.PT.KI..C.A.PFLLD.LK
D.TTK     (11-61)    NN.QSN..SVFDQLLHAETFV..TEA.EQQHLQ..KM..S...P.NT..V
D.BR-C    (12-62)    NNYQSSITSAFENL.DDEAFV..TLACEGRSIK..RV..S..P..RE.LK
M.ZF5     (11-66)    DD.KTLF.KT..EQ.LE.EF..IAIV.EDVK.R..RC..A...T.KK..
H.KUP     (4-54)     AS.SLV..QQ..MQ..EF.F..CTVAIGDVY.K..RA..A...N.KMI..I
H.LAZ-3   (12-62)    TR..ASDV.LN..RL.SRDI.I..VIV.SREQ.P..KT..M...GL.YSI.T
H.PLZF    (14-63)    PS.PTG..CKA.QM.LA.T...VIM.DSQE.H..RI.....TSM.EI..R
H.ZFPJS   (6-56)     VQ.SVRV.QEF..KQ..EK.QY..ATLD.GGLV.K..WS..AC..HF.QS.YG
H.RIC-1   (8-58)     PG.SRQ..LQ..NC.FK.F...I.EV.QNAL.R..KN..A.S.A.LKS.VV

D.GAGA    (65-117)   ..NTPCKHPVVM.AGVNANDLEA...E.V.F..EVSVDHAQ.PSL.QA..QC.NIQG
D.TTK     (62-115)   ..SHPEKHPIVI.KDVPYSDMKS..D.M.R.EVSVDQER.TAF.RV.ES.PIKG
D.BR-C    (63-116)   ..STPCKHPVIL.QDVNFMDLHA.VE.I.H.EVNVHQKS.QSF.KT.EV.RVSG
M.ZF5     (67-121)   .KLEVDSSSVIETDFLRSDI..EEV.NYM..AKISVKKEDVNLMMSSGQI.GIRF.
H.KUP     (55-108)   ..HQTSECIKIQPTDIQPDT.SY..HIM..KGPKQIVDHSRLEEGIRF.HADY
H.LAZ-3   (63-118)   DQLKCNLSVINLDPEINPED.CI..D.M..SRLNLREGNTMAVMAT.MY.QMEHV
H.PLZF    (64-114)   ....HRNSQHYT.DFLSPKT.QQI.EYA..ATLQAKAED.DDL.YA.EI..EIEY
H.ZFPJS   (57-108)   ....DGSGGSVV.PAGFAEI.EL..D.F...HLALTSGNRDQV.LA.RE..PVPEA
H.RIC-1   (59-124)   ....HDNLLNLDHDMVSPAV.RLV.DI.I.RLA.AEPS.GAV.AA.SY.QTPD.
                                                      DGAEAAAAAAVAPG
```

FIG. 2A

1   MLDTMEAPGH SRQLLLQLNN QRTKGFLCDV IIVVQNALFR AHKNVLAASS
51  AYLKSLVVHD NLLNLDHDMV SPAVFRLVLD FIYTGRLADG AEAAAAAAVA
101 PGAEPSLGAV LAAASYLQIP DLVALCKKRL KRHGKYCHLR GGGGGGGGYA
151 PYAMATSWAG SAAPPASAAK SVVGTRPSRP GGPRSAWRRR RATLAAWTGP
201 ARAATATTTR AAARRPVAAR TPAPPGGHLE GYPCPHLAYG EPESFGDNLY
251 VCIPCGKGFP SSEQLNAHVE AHVEEEEALY RCGSCDKSYK DPATLRQHEK THWLTRPYPC AHKNVLAASS
301 GGGDKVAGAP GGLGELLRPY RCGSCDKSYK DPATLRQHEK THWLTRPYPC
351 TICGKKFTQR GTMTRHMRSH LGLKPFACDA CGMRFTRQYR LTRTHMRIHP
401 RGEKPYECQV CGGKFAQQRN LISHMKMHAV GAAARPGRW RAWGGSPASP
451 APTARASSTS PRASLLWLAH GRAAEPEAAG QGGRDRAAGA DHALPARPQG
501 GAGEPLPAGQ VHGRAGPQPR QGGRGAEPGR SPGGRARRRT IDRFSPT

FIG. 2B

TUMOR SUPPRESSOR GENE, HIC-1

This is a divisional of copending application Ser. No. 08/340,203, filed Nov. 15, 1994.

This invention was made with government support under Grant No. R01-CA43318, from the National Cancer Institute. The government has certain rights in the invention.

BACKGROUND OF THE INVENTION

1. Field of the Invention

This invention relates generally to gene expression in normal and neoplastic cells, and specifically to a novel tumor suppressor gene, HIC-1, and its gene product.

2. Description of Related Art

Advances in recombinant DNA technology have led to the discovery of normal cellular genes such as proto-oncogenes and tumor suppressor genes, which control growth, development, and differentiation. Under certain circumstances, regulation of these genes is altered and they cause normal cells to assume neoplastic growth behavior. There are over 40 known proto-oncogenes and tumor suppressor genes to date, which fall into various categories depending on their functional characteristics. These include, (1) growth factors and growth factor receptors, (2) messengers of intracellular signal transduction pathways, for example, between the cytoplasm and the nucleus, and (3) regulatory proteins which influence gene expression and DNA replication (e.g., transcription factors).

Chromosome 17p is frequently altered in human cancers, and allelic losses often coincide with mutations in the p53 gene at 17p13.1 (Vogelstein, B., et al., *Cell*, 70:523, 1992). This gene is one of the most frequently altered tumor suppressor genes in human neoplasms. However, in some tumor types, 17p allelic loss occurs at a high frequency in regions distal to p53 and in the absence of p53 mutations. For instance, 60% of breast cancers lose 17p alleles while only 30% of these tumors contain p53 mutations (Chen, L-C., et al., *Proc. Natl. Acad. Sci. USA*, 88:3847, 1991; Takita, K., et al., *Cancer Res.*, 52:3914, 1992; Deng, G., et al., *Cancer Res.*, 54:499, 1994; Cornelis, R. S., et al., *Cancer Res.*, 54:4200, 1994). Furthermore, in one study of breast cancer, the independent loss of 17p13.3 alleles was accompanied by increased levels of p53 mRNA.

Human cancer cells typically contain somatically altered genomes, characterized by mutation, amplification, or deletion of critical genes. In addition, the DNA template from human cancer cells often displays somatic changes in DNA methylation (E. R. Fearon, et al., *Cell*, 61:759, 1990; P. A. Jones, et al., *Cancer Res.*, 46:461, 1986; R. Holliday, *Science*, 238:163, 1987; A. De Bustros, et al., *Proc. Natl. Acad. Sci., USA*, 85:5693, 1988); P. A. Jones, et al., *Adv. Cancer Res.*, 54:1, 1990; S. B. Baylin, et al., *Cancer Cells*, 3:383, 1991; M. Makos, et al., *Proc. Natl. Acad. Sci., USA*, 89:1929, 1992; N. Ohtani-Fujita, et al., *Oncogene*, 8:1063, 1993). However, the precise role of abnormal DNA methylation in human tumorigenesis has not been established. DNA methylases transfer methyl groups from the universal methyl donor S-adenosyl methionine to specific sites on the DNA. Several biological functions have been attributed to the methylated bases in DNA. The most established biological function is the protection of the DNA from digestion by cognate restriction enzymes. The restriction modification phenomenon has, so far, been observed only in bacteria. Mammalian cells, however, possess a different methylase that exclusively methylates cytosine residues on the DNA, that are 5' neighbors of guanine (CpG). This methylation has been shown by several lines of evidence to play a role in gene activity, cell differentiation, tumorigenesis, X-chromosome inactivation, genomic imprinting and other major biological processes (Razin, A., H., and Riggs, R. D. eds. in DNA Methylation Biochemistry and Biological Significance, Springer-Verlag, New York, 1984).

A CpG rich region, or "CpG island", has recently been identified at 17p13.3, which is aberrantly hypermethylated in multiple common types of human cancers (Makos, M., et al., *Proc. Natl. Acad. Sci. USA*, 89:1929, 1992; Makos, M., et al., *Cancer Res.*, 53:2715, 1993; Makos, M., et al., *Cancer Res.* 53:2719, 1993). This hypermethylation coincides with timing and frequency of 17p losses and p53 mutations in brain, colon, and renal cancers. Silenced gene transcription associated with hypermethylation of the normally unmethylated promoter region CpG islands has been implicated as an alternative mechanism to mutations of coding regions for inactivation of tumor suppressor genes (Baylin, S. B., et al., *Cancer Cells*, 3:383, 1991; Jones, P. A. and Buckley, J. D., *Adv. Cancer Res.*, 54:1–23, 1990). This change has now been associated with the loss of expression of VHL, a renal cancer tumor suppressor gene on 3p (J. G. Herman, et al., *Proc. Natl. Acad. Sci. USA*, 91:9700–9704, 1994), the estrogen receptor gene on 6q (Ottaviano, Y. L., et al., *Cancer Res.*, 54:2552, 1994) and the H19 gene on 11p (Steenman, M. J. C., et al., *Nature Genetics*, 7:433, 1994).

For several human tumor types, a second tumor suppressor gene may reside distal to, and be interactive with, the p53 gene at chromosome 17p13.1. There is a need to identify tumor suppressor genes in order to develop the appropriate methodologies for increasing or decreasing their expression in cells where aberrant expression is observed. Through characterization of a 17p13.3 CpG island which is aberrantly hypermethylated in multiple common human tumor types, the present invention provides such a gene. HIC-1 (hypermethylated in cancer) is a novel zinc finger transcription factor gene which is ubiquitously expressed in normal tissues, but underexpressed in tumor cells (e.g., breast, lung, colon, fibroblasts) where it is hypermethylated. A p53 binding site is located in the 5' flanking region of HIC-1. Overexpression of a wild-type p53 gene in colon cancer cells containing only a mutant p53 allele, results in 20-fold activation of HIC-1 expression.

The present invention shows that many human cancers exhibit decreased HIC-1 expression relative to their tissue of origin. The limitation and failings of the prior art to provide meaningful markers which correlate with the presence of cell proliferative disorders, such as cancer, has created a need for markers which can be used diagnostically, prognostically, and therapeutically over the course of such disorders. The present invention fulfills such a need.

SUMMARY OF THE INVENTION

The present invention is based on the seminal discovery of a novel tumor suppressor gene, HIC-1 (hypermethylated in cancer), which is aberrantly hypermethylated in multiple common human tumor types. The invention provides a HIC-1 polypeptide as well as a polynucleotide sequence encoding the polypeptide and antibodies which bind to the polypeptide.

In one embodiment, the present invention provides a diagnostic method for detecting a cell proliferative disorder associated with HIC-1 in a tissue of a subject, comprising contacting a target cellular component containing HIC-1 with a reagent which detects HIC-1. Such cellular components include nucleic acid and protein.

In another embodiment, the present invention provides a method of treating a cell proliferative disorder associated with HIC-1, comprising administering to a subject with the disorder, a therapeutically effective amount of reagent which modulates HIC-1 expression. For example, since HIC-1 associated disorders typically involve hypermethylation of HIC-1 polynucleotide sequence, a polynucleotide sequence which contains a non-methylatable nucleotide analog is utilized for treatment of a subject.

Further, the invention provides a method of gene therapy comprising introducing into cells of a host subject, an expression vector comprising a nucleotide sequence encoding HIC-1, in operable linkage with a promoter.

BRIEF DESCRIPTION OF THE DRAWINGS

FIG. 1A is a diagram showing a map of an 11.0 kb region of cosmid C-13A which contains a 50 kb human DNA insert harboring the region of chromosome 17p13.3 previously shown to have hypermethylation in multiple human tumor types (Makos, M., et al., *Proc. Natl. Acad. Sci. USA*, 89:1929, 1992; Makos, M., et al., *Cancer Res.*, 53:2715, 1993; Makos, M., et al., *Cancer Res.* 53:2719, 1993). The position of the YNZ22 probe, EcoRI (E) restriction site and the location of a series of cosmid subclones which were prepared to span the area are shown.

FIG. 1B is a schematic for the HIC-1 gene which was found to be encompassed within the region shown in FIG. 1A and for which the amino acid sequence is shown in FIG. 2B. Shown are: potential p53 binding site SEQ ID NO: 4; TATAA=the TATA box sequence 40 bp upstream from the transcription start site; 5'UTR=the 1st untranslated exon; ATG=the most 5' translation start site; ZIN (zinc finger N-terminus)=the 478 bp exon encompassing the highly conserved region (FIG. 2A) of the Zin domain subfamily of zinc finger transcription factors, rectangle with shaded bars represents the 2015 bp last exon of HIC-1 and each shaded bar represents one of the 5 zinc fingers (FIG. 2B) clustered in this 3' region of the gene; TAG=translation stop site in the HIC-1 gene; AATAAA=polyadenylation signal site found 835 bp from the translation stop site.

FIGS. 1C, 1D and 1E and SEQ ID NO: 1 and 2 show the nucleotide and deduced amino acid sequence of HIC-1.

FIG. 2A and SEQ ID NO:3 show the amino acid sequences of HIC-1. The HIC-1 amino acid sequence is compared with the conserved N-terminus region of the other members of the Zin domain zinc finger family SEQ ID NOS: 5–13. In the parentheses, the numbers indicate the position of the conserved region relative to the translation start site of each gene. The darkest shading shows position of amino acids which are identical for at least five of the 9 proteins and the lighter shading shows position of conservative amino acid differences between the family members. D=drosophilia; M=murine; H=human. The bracket of amino acids at the bottom represents an area in HIC-1 not found at this position in the other family members.

FIG. 2B shows the entire coding region of the HIC-1 gene (SEQ ID NO: 3). The deduced amino acid sequence for the two coding exons of HIC-1, as defined by the sequence analyses and expression strategies outlined in the text, are shown. The 5 zinc fingers in the 3' half of the protein are shown by the shaded boxes.

FIG. 4A compares expression in 10 ug of total RNA from 2 established culture lines of normal human fibroblasts (WI-38 and IMR-90) to the HT 1080 culture line of fibrosarcoma cells (Fibro-C), from 3 different samples of normal colon (Colon-N) to the colon carcinoma cell line, $CaCO_2$ (Colon-C), and from a sample of normal lung (Lung-N) to the established line of human small cell lung carcinoma, NCI-H209 (Lung-C).

DETAILED DESCRIPTION OF THE INVENTION

Figure 3:
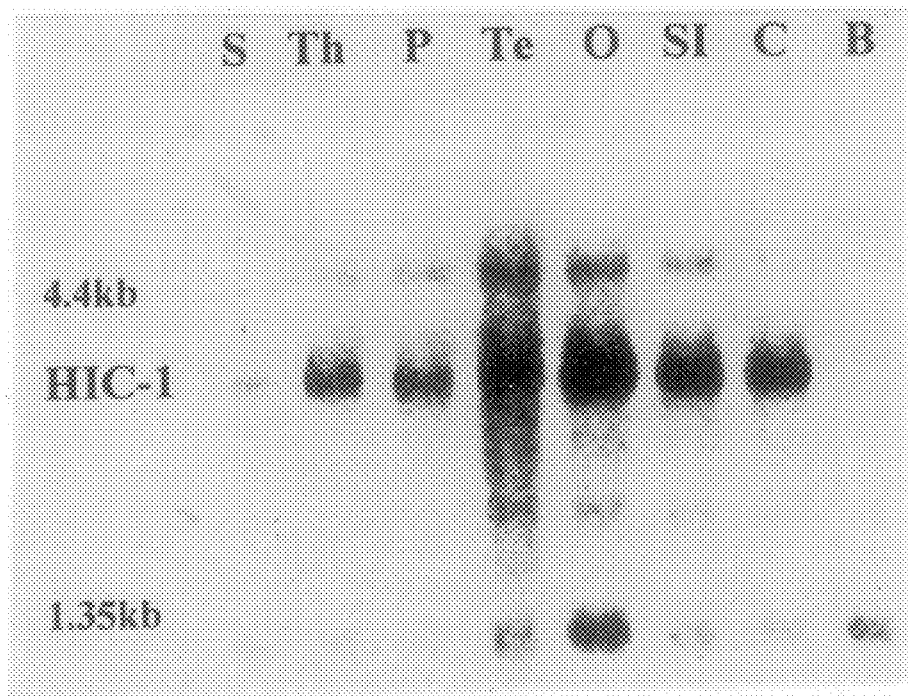
FIG. 3 shows a Northern analyses of HIC-1 gene expression. S=spleen; The=thymus; P=prostate; Te=testis; O=ovary; SI=small intestine; B=peripheral blood cells. The band above the 4.4 kb marker co-hybridizes with ribosomal RNA. The ~1.1 kb band has not yet been identified but could be an alternate splice product since it was not detected with probes from the zinc finger of 3' untranslated regions of HIC-1.

The present invention provides a novel tumor suppressor gene, HIC-1 (hypermethylated in cancer). HIC-1 is located on chromosome 17p13.3, distal to the tumor suppressor gene, p53, at 17p13.1, within a CpG island which is abnormally methylated in many different types of tumors. This abnormally methylated CpG island completely encompasses the coding region of HIC-1 gene.

In a first embodiment, the present invention provides a substantially pure HIC-1 polypeptide consisting essentially of the amino acid sequence shown in FIG. 2B and SEQ ID NO: 3. HIC-1 polypeptide is characterized as having a distinct amino acid homology to a highly conserved N-terminal motif, termed the Zin (Zinc finger N-terminal) domain, which is present in each member of subset of zinc finger transcription factors. In addition, it also has five Kruppel type $Cys_2$-$His_2$ zinc fingers characteristic of the 3' region of those same proteins.

The term "substantially pure" as used herein refers to HIC-1 polypeptide which is substantially free of other proteins, lipids, carbohydrates or other materials with which it is naturally associated. One skilled in the art can purify HIC-1 using standard techniques for protein purification. The substantially pure polypeptide will yield a single major band on a non-reducing polyacrylamide gel. The purity of the HIC-1 polypeptide can also be determined by amino-terminal amino acid sequence analysis.

The invention includes a functional polypeptide, HIC-1, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the HIC-1 polypeptide, include fragments of HIC-1 which retain the activity of e.g., tumor suppressor activity, of HIC-1. Smaller peptides containing the biological activity of HIC-1 are included in the invention. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the HIC-1 primary amino acid sequence may result in proteins which have substantially equivalent activity as compared to the HIC-1 polypeptide described herein. Such modifications may be deliberate, as by site-directed mutagenesis, or may be spontaneous. All of the polypeptides produced by these modifications are included herein as long as the tumor suppressor activity of HIC-1 is present. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for HIC-1 activity.

The HIC-1 polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides an isolated polynucleotide sequence consisting essentially of a polynucleotide sequence encoding a polypeptide having the amino acid sequence of SEQ ID NO: 3. The polynucleotide sequence of the invention also includes the 5' and 3' untranslated sequences and includes regulatory sequences, for example. The term "isolated" as used herein includes polynucleotide substantially free of other nucleic acids, proteins, lipids, carbohydrates or other materials with which it is naturally associated. Polynucleotide sequences of the invention include DNA, cDNA and RNA sequences which encode HIC-1. It is understood that all polynucleotides encoding all or a portion of HIC-1 are also included herein, as long as they encode a polypeptide with HIC-1 activity. Such polynucleotides include naturally occurring, synthetic, and intentionally manipulated polynucleotides. For example, HIC-1 polynucleotide may be subjected to site-directed mutagenesis. The polynucleotide sequence for HIC-1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of HIC-1 polypeptide encoded by the nucleotide sequence is functionally unchanged. In addition, the invention also includes a polynucleotide consisting essentially of a polynucleotide sequence encoding a polypeptide having an amino acid sequence of SEQ ID NO: 3 and having at least one epitope for an antibody immunoreactive with HIC-1 polypeptide.

The polynucleotide encoding HIC-1 includes the nucleotide sequence in FIG. 1C (SEQ ID NO: 1 and 2), as well as nucleic acid sequences complementary to that sequence. A complementary sequence may include an antisense nucleotide. When the sequence is RNA, the deoxynucleotides A, G, C, and T of FIG. 1C (SEQ ID NO: 1 and 2) are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of FIG. 2B (SEQ ID NO: 3) under physiological conditions and under moderately stringent conditions.

Specifically disclosed herein is a DNA sequence for HIC-1 which schematically is illustrated in FIGS. 1A and 1B (see also, FIG. 1C and SEQ ID NO: 2). The transcribed exon encompasses 5 zinc fingers and extends 359 bp from the last zinc finger to the stop site. The transcription proceeds 239 bp past the stop site, in an apparent 3' untranslated region (UTR). There is also a polyadenylation signal, AATAAA, at position 835 bp from the stop site. In addition, after the Zin domain and before the zinc finger exons, there is a consensus splice donor and an acceptor site separated by an intron region. The complete coding region of HIC-1 is encompassed by two exons within the CpG rich 3.0 kb region between Not I sites $N_3$ and $N_7$.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the HIC-1 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding HIC-1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of gene expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for HIC-1 peptides having at least one epitope, using antibodies specific for HIC-1. Such antibodies can be either polyclonally or monoclonally derived and used to detect expression product indicative of the presence of HIC-1 cDNA.

DNA sequences encoding HIC-1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the HIC-1 polynucleotide sequences may be inserted into a recombinant expression vector. The term "recombinant expression vector" refers to a plasmid, virus or other vehicle known in the art that has been manipulated by insertion or incorporation of the HIC-1 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segmented can be present in the vector operably linked to regulatory elements, for example, a promoter (e.g., T7, metallothionein I, or polyhedrin promoters).

Polynucleotide sequences encoding HIC-1 can be expressed in either prokaryotes or eukaryotes. Hosts can include microbial, yeast, insect and mammalian organisms. Methods of expressing DNA sequences having eukaryotic or viral sequences in prokaryotes are known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the HIC-1 coding sequence and appropriate transcriptional/ translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

A variety of host-expression vector systems may be utilized to express the HIC-1 coding sequence. These include but are not limited to microorganisms such as bacteria transformed with recombinant bacteriophage DNA, plasmid DNA or cosmid DNA expression vectors containing the HIC-1 coding sequence; yeast transformed with recombinant yeast expression vectors containing the HIC-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the HIC-1 coding sequence; insect cell systems infected with recombinant virus expression vectors (e.g., baculovirus) containing the HIC-1 coding sequence; or animal cell systems infected with recombinant virus expression vectors (e.g., retroviruses, adenovirus, vaccinia virus) containing the HIC-1 coding sequence, or transformed animal cell systems engineered for stable expression. Since HIC-1 has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses(e.g., the retrovirus long terminal repeat; the adenovirus late promoter; the vaccinia virus 7.5K promoter) may be used. Promoters produced by recombinant DNA or synthetic techniques may also be used to provide for transcription of the inserted HIC-1 coding sequence. In addition, the endogenous HIC-1 promoter may also be used to provide transcription machinery of HIC-1.

In bacterial systems a number of expression vectors may be advantageously selected depending upon the use intended for the expressed. For example, when large quantities of HIC-1 are to be produced, vectors which direct the expression of high levels of fusion protein products that are readily purified may be desirable. Those which are engineered to contain a cleavage site to aid in recovering are preferred. Such vectors include but are not limited to the *E. coli* expression vector pUR278 (Ruther, et al., *EMBO J.* 2:1791, 1983), in which the HIC-1 coding sequence may be ligated into the vector in frame with the lac Z coding region so that a hybrid -lac Z protein is produced; pIN vectors (Inouye & Inouye, *Nucleic Acids Res.*, 13:3101–3109, 1985; Van Heeke & Schuster, J. Biol. Chem. 264:5503–5509, 1989); glutathione-S-transferase (GST) and the like.

In yeast, a number of vectors containing constitutive or inducible promoters may be used. For a review see, *Current Protocols in Molecular Biology,* Vol. 2, 1988, Ed. Ausubel, et al., Green Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C., Ch. 3; and Bitter, 1987, *Heterologous Gene Expression in Yeast, Methods in Enzymology,* Eds. Berger & Kimmel, Acad. Press, N.Y., Vol. 152, pp. 673–684; and *The Molecular Biology of the Yeast Saccharomyces,* 1982, Eds. Strathern, et al., Cold Spring Harbor Press, Vols. I and II. A constitutive yeast promoter such as ADH or LEU2 or an inducible promoter such as GAL may be used (*Cloning in Yeast,* Ch. 3, R. Rothstein In: DNA Cloning Vol.11, A Practical Approach, Ed. DM Glover, 1986, IRL Press, Wash., D.C.). Alternatively, vectors may be used which promote integration of foreign DNA sequences into the yeast chromosome.

In cases where plant expression of the HIC-1 coding sequence may be driven by any of a number of promoters. For example, viral promoters such as the 35S RNA and 19S RNA promoters of CaMV (Brisson, et al., *Nature* 310:511–514, 1984), or the coat protein promoter to TMV (Takamatsu, et al., *EMBO J.*6:307–311, 1987) may be used; alternatively, plant promoters such as the small subunit of RUBISCO (Coruzzi, et al., *EMBO J.*3:1671–1680, 1984; Broglie, et al., *Science* 224:838–843, 1984); or heat shock promoters, e.g., soybean hsp17.5-E or hsp17.3-B (Gurley, et al., *Mol. Cell. Biol.* 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology,* Academic Press, N.Y., Section VIII, pp. 421–463; and Grierson & Corey, 1988, *Plant Molecular Biology,* 2d Ed., Blackie, London, Ch. 7–9.

An alternative expression system which could be used to express is an insect system. In one such system, *Autographa californica* nuclear polyhedrosis virus (AcNPV) is used as a vector to express foreign genes. The virus grows in *Spodoptera frugiperda* cells. The HIC-1 coding sequence may be cloned into non-essential regions (for example the polyhedrin gene) of the virus and placed under control of an AcNPV promoter (for example the polyhedrin promoter). Successful insertion of the HIC-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, *J. Viol.* 46:584; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of HIC-1. Mammalian cell lines may be preferable. Such host cell lines may include but are not limited to CHO, VERO, BHK, HeLa, COS, MDCK, -293, and W138.

Mammalian cell systems which utilize recombinant viruses or viral elements to direct expression may be engineered. For example, when using adenovirus expression vectors, the HIC-1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see Logan & Shenk, *Proc. Natl. Acad. Sci. USA,* 81:3655–3659, 1984). Alternatively, the vaccinia virus 7.5K promoter may be used (e.g., see, Mackett, et al., 1982, *Proc. Natl. Acad. Sci. USA* 79:7415–7419; Mackett, et al., *J. Virol.* 49:857–864, 1984; Panicali, et al., *Proc. Natl. Acad. Sci. USA* 79:4927–4931, 1982). Of particular interest are vectors based on bovine papilloma virus which have the ability to replicate as extra-chromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the HIC-1 gene in host cells (Cone & Mulligan, *Proc. Natl. Acad. Sci. USA* 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the HIC-1 cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell,* 11:223, 1977), hypoxanthine-guanine phosphoribosyltransferase (Szybalska & Szybalski, *Proc.*

*Natl. Acad. Sci. USA,* 48:2026, 1962), and adenine phosphoribosyltransferase (Lowy, et al., *Cell,* 22: 817, 1980) genese can be employed in tk⁻, hgprt⁻ or aprt⁻ cells respectively. Also, antimetabolite resistance can be used as the basis of selection for dhfr, which confers resistance to methotrexate (Wigler, et al., *Natl. Acad. Sci. USA,* 77:3567, 1980; O'Hare, et al., *Proc. Natl. Acad. Sci. USA,* 78: 1527, 1981); gpt, which confers resistance to mycophenolic acid (Mulligan & Berg, *Proc. Natl. Acad. Sci. USA,* 78: 2072, 1981; neo which confers resistance to the aminoglycoside G-418 (Colberre-Garapin, et al., *J. Mol. Biol.,* 150:1, 1981); and hygro, which confers resistance to hygromycin (Santerre, et al., *Gene,* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA,* 85:8047, 1988); and ODC (ornithine decarboxylase) which confers resistance to the ornithine decarboxylase inhibitor, 2-(difluoromethyl)-DL-ornithine, DFMO (McConlogue L., 1987, In: *Current Communications in Molecular Biology,* Cold Spring Harbor Laboratory, ed.).

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the HIC-1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman, ed., 1982).

Isolation and purification of microbial or host cell expressed polypeptide, or fragments thereof, provided by the invention, may be carried out by conventional means including preparative chromatography and affinity and immunological separations involving monoclonal or polyclonal antibodies.

The invention includes antibodies immunoreactive with HIC-1 polypeptide (SEQ ID NO: 3) or immunoreactive fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and $F(ab')_2$, which are capable of binding an epitopic determinant on HIC-1.

The invention also provides a method for detecting a cell proliferative disorder associated with HIC-1 in a subject, comprising contacting a target cellular component suspected of having a HIC-1 associated disorder, with a reagent which reacts with or binds to HIC-1 and detecting HIC-1. The target cell component can be nucleic acid, such as DNA or RNA, or it can be protein. When the component is nucleic acid, the reagent is typically a nucleic acid probe or PCR primer. When the cell component is protein, the reagent is typically an antibody probe. The target cell component may be detected directly in situ or it may be isolated from other cell components by common methods known to those of skill in the art before contacting with a probe. (See for example, Maniatis, et al., *Molecular Cloning, A Laboratory Manual,* Cold Spring Harbor Laboratory, N.Y. 1989; *Current Protocols in Molecular Biology,* 1994, Ed. Ausubel, et al., Green Publ. Assoc. & Wiley Interscience.) Detection methods include Southern and Northern blot analyses, RNase protection, immunoassays and other detection assays that are known to those of skill in the art.

The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probes or will be able to ascertain such, using routine experimentation.

Since the present invention shows that a decreased level of HIC-1 transcription is often the result of hypermethylation of the HIC-1 gene, it is often desirable to directly determine whether the HIC-1 gene is hypermethylated. In particular, the cytosine rich areas terms "CpG islands" which lie in the 5' regulatory regions of genes are normally unmethylated. The term "hypermethylation" includes any methylation of cytosine which is normally unmethylated in the HIC-1 gene sequence can be detected by restriction endonuclease treatment of HIC-1 polynucleotide (gene) and Southern blot analysis for example. Therefore, in a method of the invention, when the cellular component detected is DNA, restriction endonuclease analysis is preferable to detect hypermethylation of the HIC-1 gene. Any restriction endonuclease that includes CG as part of its recognition site and that is inhibited when the C is methylated, can be utilized. Methylation sensitive restriction endonucleases such as BssHII, MspI, NotI or HpaII, used alone or in combination are examples of such endonucleases. Other methylation sensitive restriction endonucleases will be known to those of skill in the art. In addition, PCR can be utilized to detect the methylation status of the HIC-1 gene. Oligonucleotide primers based on any coding sequence region in the HIC-1 sequence are useful for amplyifying DNA by PCR.

For purposes of the invention, an antibody or nucleic acid probe specific for HIC-1 may be used to detect the presence of HIC-1 polypeptide (using antibody) or polynucleotide (using nucleic acid probe) in biological fluids or tissues. Oligonucleotide primers based on any coding sequence region in the HIC-1 sequence are useful for amplifying DNA, for example by PCR. Any specimen containing a detectable amount of HIC-1 polynucleotide or HIC-1 polypeptide antigen can be used. Nucleic acid can also be analyzed by RNA in situ methods which are known to those of skill in the art. A preferred sample of this invention is tissue of heart, renal, brain, colon, breast, urogenital, uterine, hematopoietic, prostate, thymus, lung, testis, and ovarian. Preferably the subject is human.

Various disorders which are detectable by the method of the invention include astrocytoma, anaplastic astrocytoma, glioblastoma, medulloblastoma, colon cancer, lung cancer, renal cancer, leukemia, breast cancer, prostate cancer, endometrial cancer and neuroblastoma.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of HIC-1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-HIC-1 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 $\mu g/\mu l$) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the HIC-1 antigen for which the monoclonal antibodies are specific. The concentration of detectably labeled monoclonal antibody which is administered should be sufficient such that the binding to those cells having HIC-1 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have al type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentactic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The present invention also provides a method for treating a subject with a cell proliferative disorder associated with of HIC-1 comprising administering to a subject with the disorder a therapeutically effective amount of reagent which modulates HIC-1 expression. In brain, breast and renal cancer cells, for example, the HIC-1 nucleotide sequence is under-expressed as compared to expression in a normal cell, therefore, it is possible to design appropriate therapeutic or diagnostic techniques directed to this sequence. Thus, where a cell-proliferative disorder is associated with the expression of HIC-1 associated with malignancy, nucleic acid sequences that modulate HIC-1 expression at the transcriptional or translational level can be used. In cases when a cell proliferative disorder or abnormal cell phenotype is associated with the under expression of HIC-1, for example, nucleic acid sequences encoding HIC-1 (sense) could be administered to the subject with the disorder.

The term "cell-proliferative disorder" denotes malignant as well as non-malignant cell populations which often appear to differ from the surrounding tissue both morphologically and genotypically. Such disorders may be associated, for example, with absence of expression of HIC-1. Essentially, any disorder which is etiologically linked to expression of HIC-1 could be considered susceptible to treatment with a reagent of the invention which modulates HIC-1 expression.

The term "modulate" envisions the suppression of methylation of HIC-1 polynucleotide when HIC-1 is underexpressed. When a cell proliferative disorder is associated with HIC-1 expression, such methylation suppressive reagents as 5-azacytadine can be introduced to a cell. Alternatively, when a cell proliferative disorder is associated with under-expression of HIC-1 polypeptide, a sense polynucleotide sequence (the DNA coding strand) encoding HIC-1 polypeptide, or 5' regulatory nucleotide sequences (i.e., promoter) of HIC-1 in operable linkage with HIC-1 polynucleotide can be introduced into the cell. Demethylases known in the art could also be used to remove methylation.

The present invention also provides gene therapy for the treatment of cell proliferative disorders which are mediated by HIC-1. Such therapy would achieve its therapeutic effect by introduction of the appropriate HIC-1 polynucleotide which contains a HIC-1 structural gene (sense), into cells of subjects having the proliferative disorder. Delivery of sense HIC-1 polynucleotide constructs can be achieved using a recombinant expression vector such as a chimeric virus or a colloidal dispersion system.

The polynucleotide sequences used in the method of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense structural gene for HIC-1 or sense promoter for HIC-1 operably linked to HIC-1 structural gene.

In another embodiment, a HIC-1 structural gene is operably linked to a tissue specific heterologous promoter and used for gene therapy. For example, a HIC-1 gene can be ligated to prostate specific antigen (PSA)-prostate specific promoter for expression of HIC-1 in prostate tissue. Other tissue specific promoters will be known to those of skill in the art. Alternatively, the promoter for another tumor suppressor gene can be linked to the HIC-1 structural gene and used for gene therapy.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Most preferably, a non-human primate retroviral vector is employed, such as the gibbon ape leukemia virus (GaLV), thereby providing a broader host range than murine vectors, for example.

A number of additional retroviral vectors can incorporate multiple genes. All of these vectors can transfer or incorporate a gene for a selectable marker so that transduced cells can be identified and generated. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the HIC-1 sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\Psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for HIC-1 polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting HIC-1 antibody-containing liposomes directly to the malignant tumor. Since the HIC-1 gene product may be indiscriminate with respect to cell type in its action, a targeted delivery system offers a significant improvement over randomly injecting non-specific liposomes. Preferably, the target tissue is human brain, colon, breast, lung, and renal origin. A number of procedures can be used to covalently attach either polyclonal or monoclonal antibodies to a liposome bilayer. Antibody-targeted liposomes can include monoclonal or polyclonal antibodies or fragments thereof such as Fab, or $F(ab')_2$, as long as they bind efficiently to an antigenic epitope on the target cells. Liposomes may also be targeted to cells expressing receptors for hormones or other serum factors.

For use in the diagnostic research and therapeutic applications suggested above, kits are also provided by the invention. Such a kit may comprise a carrier means being compartmentalized to receive in close confinement one or more container means such as vials, tubes, and the like, each of the container means comprising one of the separate elements to be used in the method.

For example, one of the container means may comprise a probe which is or can be detectably labelled. Such probe may be an antibody or nucleotide specific for a target protein or a target nucleic acid, respectively, wherein the target is indicative, or correlates with, the presence of HIC-1 of the invention. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionucleotide label.

The invention also provides a method for identifying a tumor suppressor gene by detecting abnormal nucleic acid methylation, in particular, detecting CpG island hypermethylation in the regions of frequent allelic loss. The present invention has shown that aberrant methylation of normally unmethylated CpG islands can function as a "mutation" to silence tumor suppressor gene transcription during tumor progression. The occurrence of the 17p13.3 hypermethylation appears to correlate with both the timing and incidence of these allelic losses in the progression of brain, colon, and renal cancers. It is shown by the present invention that this CpG island harbors a tumor suppressor HIC-1 gene which is silenced by abnormal methylation. In other words, identification of such CpG islands has constituted an important strategy for isolation of the new tumor suppressor HIC-1 gene. Therefore, the finding of this abnormality in chromosome areas which frequently undergo the tumor associated allelic losses that broadly define candidate tumor suppressor regions could facilitate the localization of the responsible genes. The common methods used for detecting abnormal nucleic acid methylation are well known in the art and those skilled in the art should be able to use one of the methods accordingly for the purpose of practicing the present invention.

The following Examples are intended to illustrate, but not to limit the invention. While such Examples are typical of those that might be used, other procedures known to those skilled in the art may alternatively be utilized.

EXAMPLES

HIC-1 expression is ubiquitous in normal adult tissues. However, in cultured tumor cells and in primary cancers which exhibit hypermethylation of the associated CpG island, HIC-1 expression is reduced or absent. For example, the expression of HIC-1 is absent in tumors with CpG island hypermethylation, including lung, colon, breast and brain tumors. This expression pattern is consistent with a tumor suppressor gene function for HIC-1.

Example 1

Materials and Methods

1. Subcloning of Cosmid DNA

Subclones of cosmid C13A DNA (FIG. 1A) were prepared by isolation of multiple restriction fragments on agarose gels and ligation of these into pBluescript plasmid (Stratagene).

2. DNA Sequencing

Single stranded DNA was first isolated by growing plasmid DNA in 2×YT broth with 75 ug/ml ampicillin and in the presence of $10^7$–$10^8$ pfu/ml of VCSM13 (Stratagene) (helper phage) for 2 hrs. After isolation, the DNA was sequenced using the GIBCO BRL cycle sequencing kit. Generally, 22 base pair primers were end labeled with $\gamma$-$^{32}$P and cycle conditions were 95° C. for 1 cycle followed by 20 cycles of 95° C. for 10 sec. and 65° C. for 10 sec. Reaction products were analyzed on 10% acrylamide/8M urea gels.

3. Southern and Northern Hybridizations

Isolation procedures for DNA and poly A+RNA, agarose gel running conditions, $\alpha$-$^{32}$P labelling of probes, filter hybridization and wash conditions are as previously described (Baylin, S. B., et al., *Cancer Cells,* 3:383–390, 1991; Jones, P. A., et al., *Cancer Res.* 54:1–23, 1990; Herman, J. G., et al., *Proc. Nat'l Acad. Sci.,* in press, 1994; Ottaviano, Y. L., et al., *Cancer Res.,* 54:2552–2555, 1994;

Issa, J-P., et al., *Nature Genetics*, in press; Steenman, M. J. C., et al., *Nature Genetics*, 7:433–439, 1994; and Gish, W., et al., *Nature Genetics*, 3:266–272, 1993). Radioautograms were either exposed at −70° C. for various times or in a phosphoimager casette, followed by exposure and analysis in the phosphoimager Image Quant program (Molecular Dynamics). Preparation of single strand, $\alpha$-$^{32}$P-labeled RNA probes for use in some Northern hybridizations was accomplished by in vitro transcription, using $T_3$ or $T_7$ polymerase, of DNA inserts in the various cosmid subclones shown in FIG. 1A.

4. RNAse Protection Assays

Preparation of $\alpha$-$^{32}$P-labeled RNA probes from the various cosmid subclones (FIG. 1A), liquid hybridization to RNA samples, and post-hybridization digestion by RNAse were all performed with the Ambion MAXIscript and RPAII kits according to the manufacturer's specifications. In general, $8\times10^4$ cpm of probe was hybridized to 10 μg of total RNA for 12–15 h at 45° C. Products of RNAse digestion were analyzed on a 6% acrylamide/8M urea gel. Lengths of hybridization probes were determined by positions of various restriction cuts of the plasmid insert DNA. For assessment of RNA loading, a 250 bp GAPDH probe was prepared by Hinc II restriction and co-hybridized with RNA in all reactions.

5. Exon Trapping

Exon trapping was performed with subclone 26 (FIG. 1A) using the GIBCO BRL Exon Trapping System, as per manufacturer's protocol.

6. Cell Cultures and Tissue Specimens

Normal human fibroblast lines WI-38 and IMR-90 and colon cancer line, $CaCO_2$, were obtained from the American Tissue Culture Collection (ATCC, Rockville, Md.). The NCI-H209 line of human small cell lung carcinoma has been previously described (Carney, D. N., et al., *Recent Results Cancer Res.*, 99:157–166, 1985). All established breast cancer lines were utilized, as detailed in FIG. 5, in a recent study (Herman, J. G., et al., *Proc. Nat'l. Acad. Sci.*, 91:9700–9704, 1994) and were kindly provided by Dr. Nancy Davidson. A cell fusion system of tumor progression consisting of normal donor fibroblast line GM229 and the HT1080 line of fibrosarcoma cells, plus their fusion products, SFTH300 and SFTH300TR1, were a gift from Dr. B. Weismann. All samples of fresh, non-cultured, normal and neoplastic human tissues were those obtained as described (Herman, J. G, et al, supra; Ottaviano, Y. L., et al., supra; Issa, J-P., et al., supra; Steenman, M. J. C., et al., supra; and Gish, W., et al., supra).

Example 2

Identification of New Tumor Suppressor Gene

To characterize the region encompassing the aberrantly methylated CpG island, a series of subclones were prepared (FIG. 1A) from the 17p cosmid C-13A (Ledbetter, D. H., et al., *Proc. Natl. Acad. Sci. USA*, 86:5136, 1989; El-Deiry, W. S., et al., *Nature Genetics*, 1:45–49, 1992; Kern, S. E., et al., *Science*, 252:1708, 1991; Funk, W. D., et al., *Mol. & Cell. Biol.*, 12:2866, 1992) previously shown to contain the cluster of methylation sensitive Not I sites hypermethylated in tumors. Using these as probes for "zoo blots", three regions (FIG. 1A: plasmids CI, CII, and 400) were found which hybridized, under stringent conditions, to restriction fragments in bovine and murine DNA. Traditional positional cloning approaches were impeded by high non-specific hybridization of these probes to human DNA and cDNA libraries, probably due to the high GC content of the area. Therefore, most of the 11 kb region (FIG. 1A) was sequenced and analyzed by the Grail computer program (Gish, W., et al., D. J., *Nature Genetics*, 3:266, 1993).

FIG. 1A is a diagram showing a map of an 11.0 kb region of cosmid C-13A which contains a 50 kb human DNA insert harboring the region of chromosome 17p13.3 previously shown to have hypermethylation in multiple human tumor types (Makos, M., et al., *Proc. Natl. Acad. Sci. USA*, 89:1929, 1992; Makos, M., et al., *Cancer Res.*, 53:2715, 1993; Makos, M., et al., *Cancer Res.* 53:2719, 1993). The position of the YNZ22 probe, EcoRI (E) restriction site and the location of a series of cosmid subclones which were prepared to span the area are shown.

FIG. 1B is a schematic for the HIC-1 gene which was found to be encompassed within the region shown in FIG. 1A and for which the amino acid sequence is shown in FIG. 2B. Shown are: potential p53 binding site; TATAA=the TATA box sequence 40 bp upstream from the transcription start site; 5'UTR=the 1st untranslated exon; ATG=the most 5' translation start site; ZIN (zinc finger N-terminus)=the 478 bp exon encompassing the highly conserved region (FIG. 2A) of the Zin domain subfamily of zinc finger transcription factors; rectangle with shaded bars represents the 2015 bp last exon of HIC-1 and each shaded bar represents one of the 5 zinc fingers (FIG. 2B) clustered in this 3' region of the gene; TAG=translation stop site in the HIC-1 gene; AATAAA=polyadenylation signal site found 835 bp from the translation stop site. FIG. 1C shows the nucleotide and deduced amino acid sequence of HIC-1 (SEQ ID NO: 1).

Two independent regions of excellent coding potential were revealed between the $N_3$ to $N_7$ Not I restriction sites (FIG. 1A). Blast program (Altschul, S. F., et al., *J. Mol. Biol.*, 215:403, 1990) analysis revealed distinct amino acid homologies (FIGS. 1B and 2A), within one of the independent regions to a highly conserved N-terminal motif, termed the Zin (zinc finger N-terminal) domain (SEQ ID NOS: 5–13), which is present in each member of a recently defined subset of zinc finger transcription factors (Harrison and Travers, *EMBO J* 9:207, 1990; di Bello, et al., *Genetics*, 129:385, 1991; Numoto, et al., *Nucleic Acids Res.* 21:3767, 1993; Chardin, et al., *Nucleic Acids Res.* 19:1431, 1991). In addition to the Zin domain, five Kruppel type $Cys_2$-$His_2$ zinc fingers (Ruppert, J. M., et al., *Mol. & Cell. Biol.*, 8:3104–3113, 1988) characteristic of the 3' region of these same proteins, were also identified (FIGS. 1B and 2B). This novel gene was named HIC-1 (hypermethylated in cancer).

Example 3

Characterization of HIC-1

A combination of RNAse protection strategies, exon trapping studies, and Northern blot analyses, were utilized to characterize expression of HIC-1 and to define the genomic structure of the gene (FIGS. 1B and 1C; SEQ ID NO: 1 and 2). The start of transcription was identified within 40 bp downstream from a TATA box sequence (FIG. 1B) which precedes an untranslated first exon. The putative ATG site and the Zin domain are located in a 476 bp second exon and are in a similar position to those of the 8 other Zin domain proteins (FIG. 2A). The 5 zinc fingers (FIGS. 1B and 2B) reside in a 2015 bp final exon, containing a translation stop site 835 bp upstream from the polyadenylation signal, AATAAA. The HIC-1 gene (FIGS 1C and 2B), structured similarly to the other Zin domain proteins, is encompassed by three exons within the CpG rich 3.0 kb region between Not I sites $N_3$ and $N_7$ (FIG. 1).

FIG. 2A and SEQ ID NO: 2 show the amino acid sequences of HIC-1. The HIC-1 amino acid sequence is compared with the conserved N-terminus region of the other members of the Zin domain zinc finger family. In the parentheses, the numbers indicate the position of the conserved region relative to the translation start site of each gene. The darkest shading shows position of amino acids which are identical for at least five of the 9 proteins and the lighter shading shows position of conservative amino acid differences between the family members. D=drosophila; M=murine; H=human. The bracket of amino acids at the bottom represents an area in HIC-1 not found at this position in the other family members.

FIG. 2B and SEQ ID NO: 3 show the entire coding region of the HIC-1 gene. The deduced amino acid sequence for the two coding exons of HIC-1, as defined by the sequence analyses and expression strategies outlined in the text, are shown. The 5 zinc fingers in the 3' half of the protein are shown by the shaded boxes.

Example 4

Analysis of HIC-1 Gene Expression

HIC-1 was found to be ubiquitously expressed gene. By Northern analysis of poly A+ RNA from multiple normal tissues, probes from the HIC-1 Zin domain, zinc finger regions, and 3' untranslated regions inclusive of the polyadenylation site, all identified the same predominant 3.0 kb transcript. FIG. 3 shows a Northern analyses of HIC-1 gene expression. S=spleen; The=thymus; P=prostate; Te=testis; O=ovary; SI=small intestine; B=peripheral blood cells. The band above the 4.4 kb marker co-hybridizes with ribosomal RNA. The ~1.1 kb band has not yet been identified but could be an alternate splice product since it was not detected with probes from the zinc finger or 3' untranslated regions of HIC-1.

Figure 4A:
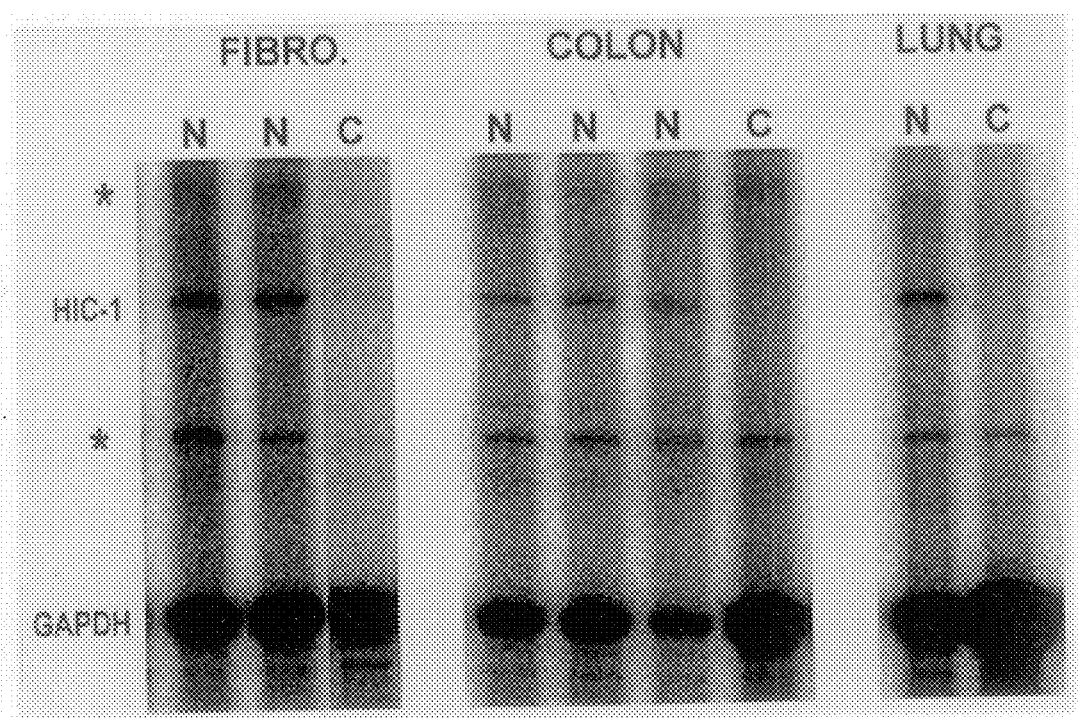
FIG. 4A shows RNAse protection assays of HIC-1 gene expression in a variety of normal and neoplastic human tissues. In all panels, the top asterisk marks the position of the undigested 360 bp HIC-1 gene RNA probe which was derived from the region containing the zinc fingers in cosmid subclone 600 (FIG. 1A). The protected HIC-1 fragment (300 bp) is labeled HIC-1.

FIG. 4A shows RNAse protection assays of HIC-1 gene expression in a variety of normal and neoplastic human tissues. In all panels, the top asterisk marks the position of the undigested 360 bp HIC-1 gene RNA probe which was derived from the region containing the zinc fingers in cosmid subclone 600 (FIG. 1A). The protected HIC-1 fragment (300 bp) is labeled HIC-1. FIG. 4A compares expression in 10 ug of total RNA from 2 established culture lines of normal human fibroblasts (WI-38 and IMR-90) to the HT 1080 culture line of fibrosarcoma cells (Fibro-C), from 3 different samples of normal colon (Colon-N) to the colon carcinoma cell line, $CaCO_2$ (Colon-C), and from a sample of normal lung (Lung-N) to the established line of human small cell lung carcinoma, NCI-H209 (Lung-C).

Figure 4B:
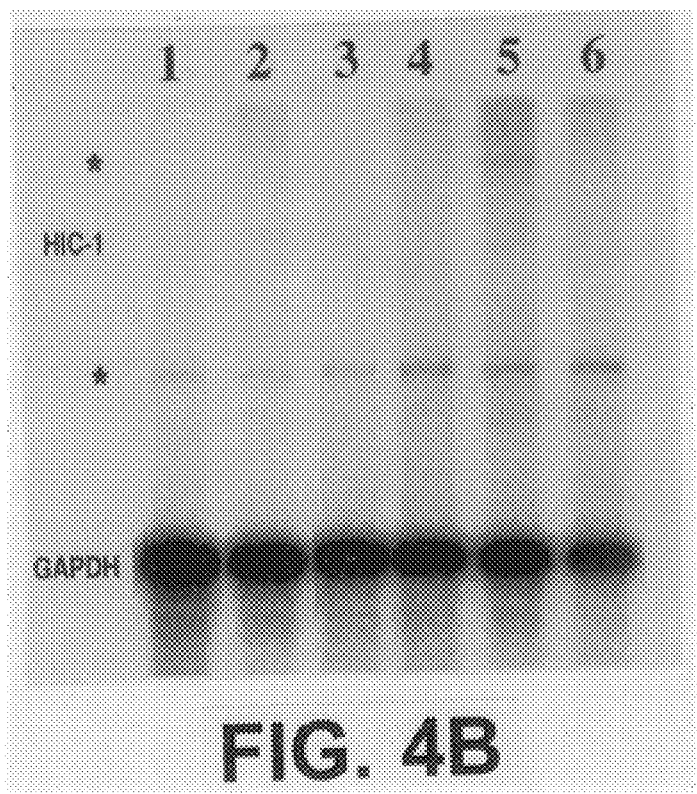
FIG. 4B shows the RNAse protection assay for 10 ug of RNA from 6 different established culture lines of breast carcinoma (lane 1 MDA231; lane 2 HS58T; lane 3 MDA468; lane 4 T47D; lane 5 MCF7; lane 6 MDA453), each of which has extensive methylation of Not I sites of the HIC-1 CpG island.
Figure 4C:
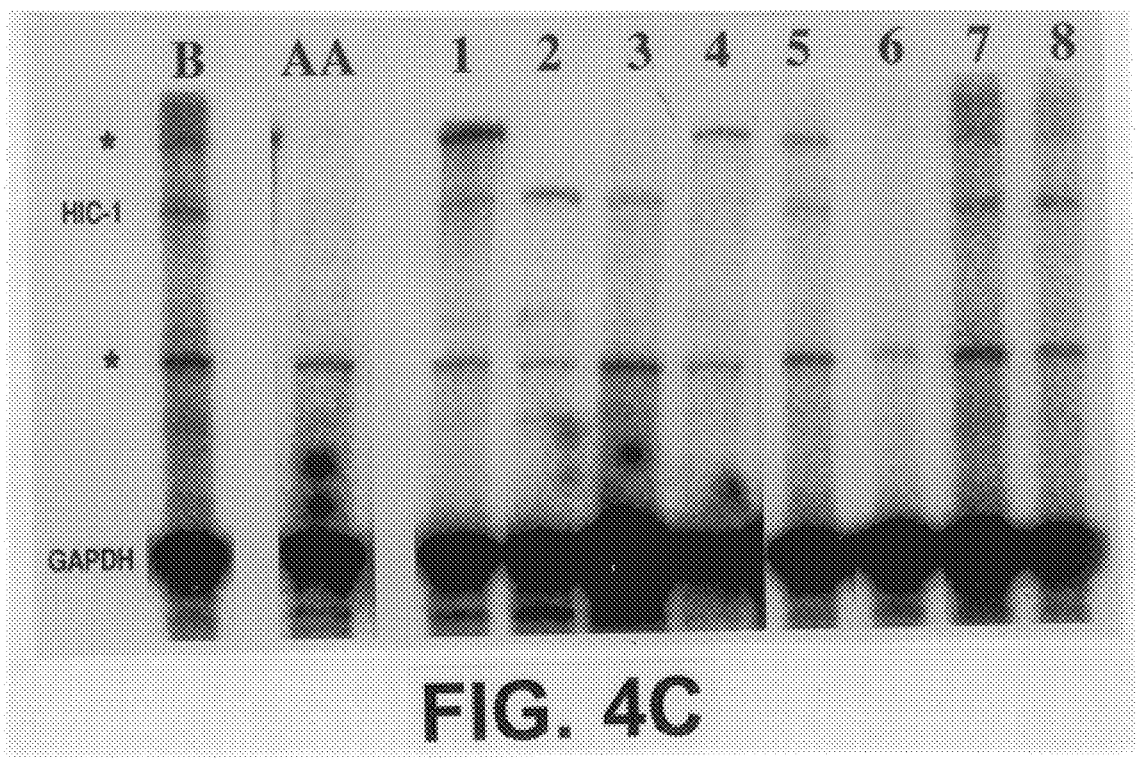
FIG. 4C shows the RNAse protection assay for 10 ug of RNA from normal fetal brain (B) compared to a series of non-cultured brain tumors (1 anaplastic astrocytoma (AA) and 8 more advanced glioblastomas (lanes 1–8).

FIG. 4B shows the RNAse protection assay for 10 ug of RNA from 6 different established culture lines of breast carcinoma (lane 1 MDA231; lane 2 HS58T; lane 3 MDA468; lane 4 T47D; lane 5 MCF7; lane 6 MDA453), each of which has extensive methylation of Not I sites of the HIC-1 CpG island. FIG. 4C shows the RNAse protection assay for 10 ug of RNA from normal fetal brain (B) compared to a series of non-cultured brain tumors (1 anaplastic astrocytoma (AA) and 8 more advanced glioblastomas (lanes 1–8).

The 3.0 kb transcript was found in all adult tissues tested with especially high levels in lung, colon, prostate, thymus, testis, and ovary (FIG. 3). With the Zin domain probe, a 1.1 kb transcript was also detected in some tissues which may represent an alternatively spliced product (FIG. 3). RNAse protection assays (RPAZ Kit-Ambion), using a probe from plasmid 600 (FIG. 1A), validated the ubiquitous expression of HIC-1, protecting transcripts of predicted size in cultured fibroblasts (FIG. 4A) and non-cultured colon mucosa (FIG. 4A), lung (FIG. 4A), and brain (FIG. 4C).

By RNAse protection assays, HIC-1 expression was found to be absent or decreased in neoplastic cells which have aberrant HIC-1 CpG island methylation. Little or no expression (FIG. 4A) was detected in cultured cancer cell lines of colon, lung, and fibroblast, all previously shown to be fully methylated at Not I sites 3 through 7. The same finding was true for 6 cultured breast cancers (FIG. 4B), all of which exhibited hypermethylation of Not I sites 3 through 7.

Furthermore, in primary colon tumors, HIC-1 expression was 2 to 17-fold decreased in a non-cultured human colon polyp and 3 primary colon tumors, as compared to the corresponding normal colon. Finally, the absence of HIC-1 expression in primary, non-cultured brain tumors was found in tumors that exhibited aberrant hypermethylation of the CpG island. An anaplastic astrocytoma which exhibited a full methylation pattern of the HIC-1 CpG island, did not express this gene (FIG. 4C), as compared to normal brain. In 4 glioblastomas, in which both DNA and RNA were available, two expressed HIC-1 either weakly (FIG. 4C, lane 1) or not at all (FIG. 4C, lane 4) and had predominantly hypermethylated alleles, while two with unmethylated alleles expressed the gene at levels equal to adjacent normal brain (FIG. 4C, lanes 2 and 3).

Four additional glioblastomas for which RNA was available were also studied. One expressed HIC-1 weakly (FIG. 4C, lane 5), one had no expression (FIG. 4C, lane 6), and two tumors expressed this gene (FIG. 4C, lanes 7–8).

In addition, hypermethylation of HIC-1 was analyzed in several primary tumors and cultured cell lines by DNA analysis as follows. Southern analyses of DNA from control and 24 hour infected cells which was digested with EcoRI (12 U/ug DNA) plus Not I (20 U/ug), were probed with $\alpha$-$^{32}$P-labeled YNZ22 (FIG. 1A) exactly as detailed in previous studies (Makos, et al., supra, 1992, 1993). Filters were imaged in the Phospho-imager (Molecular Dynamics). The results shown in Table 1 indicate that HIC-1 is found to be hypermethylated in a variety of tumors and cell lines from various origins including brain, colon, renal, hematopoietic, and prostate cancers and tumors.

TABLE 1

HYPERMETHYLATION OF HIC-1 IN TUMORS AND CELL LINES

| | PRIMARY TUMORS | | | CULTURED CELL LINES | | |
|---|---|---|---|---|---|---|
| | # | METH | % | | # | METH | % |
| BRAIN TUMORS | | | | | | |
| Low Grade Astrocytomas | 7 | 7 | 100 | | | |
| Anaplastic Astrocytomas | 5 | 4 | 80 | | | |
| Glioblastoma Multiforme | 8 | 6 | 75 | Glials | 2 | 2 | 100 |
| Medulloblastoma | 5 | 4 | 80 | | | |
| COLON | | | | | | |

TABLE 1-continued

HYPERMETHYLATION OF HIC-1 IN TUMORS AND CELL LINES

| PRIMARY TUMORS | | | | CULTURED CELL LINES | | | |
|---|---|---|---|---|---|---|---|
| | # | METH | % | | # | METH | % |
| CANCERS | | | | | | | |
| Polyps | 6 | 6 | 100 | | | | |
| Carcinomas | 8 | 7 | 90 | Carcinoma | 6 | 7 | 85 |
| LUNG CANCERS | | | | | | | |
| Carcinomas | 5 | 0 | 0 | Carcinoma | 16 | 12 | 75 |
| RENAL CANCERS | | | | | | | |
| Early Stage | 8 | 4 | 50 | | | | |
| Late Stage | 3 | 2 | 67 | Late Stage | 21 | 16 | 80 |
| LEU-KEMIAS | | | | | | | |
| Lymphomas | 3 | 1 | 33 | Lympho-mas | 8 | 5 | 60 |
| CML/Blast | 8 | 7 | 87 | | | | |
| AML | 13 | 10 | 80 | | | | |
| ALL | 10 | 8 | 80 | | | | |
| BREAST CANCERS | | | | | | | |
| Cancer | 24 | 15 | 62 | Cancers | 6 | 6 | 100 |
| PROSTATE CANCERS | | | | | | | |
| Cancer | 17 | 17 | 100 | Cancer | 5 | 4 | 80 |
| ENDOMETRIAL CANCER | | | | | | | |
| Cancer | 6 | 4 | 67 | | | | |
| NEURO-BLASTOMAS | | | | | | | |
| early/late stage (amount of methylation LOW) | 12 | 2 | 16 | Cancers | 4 | 4 | 100 |

Example 5

Interaction of P53 with HIC-1 Expression

Consistent with the hypothesis that a suppressor gene exists at 17p13.3 which may interact with p53, the present invention identifies a potential p53 binding site 4 kg 5' to the TATA box in the HIC-1 gene (FIG. 1B). Therefore, the p53 response of the HIC-1 gene was tested by using a colon cancer cell line (SW480) in which the p53 responsive gene, WAF-1; had been shown previously to be induced by expression of wild type p53 (El-Deiry, et al., Cell, 75:817–825, 1993). This cell line contains one 17p chromosome, a mutant p53 allele, and a fully methylated HIC-1 CpG island. Furthermore, the cell line SW480 is severely growth arrested by exogenously expressing the wild type p53 gene (Baker, S. J., et al., Science, 249:912–915, 1990).

Figure 5:
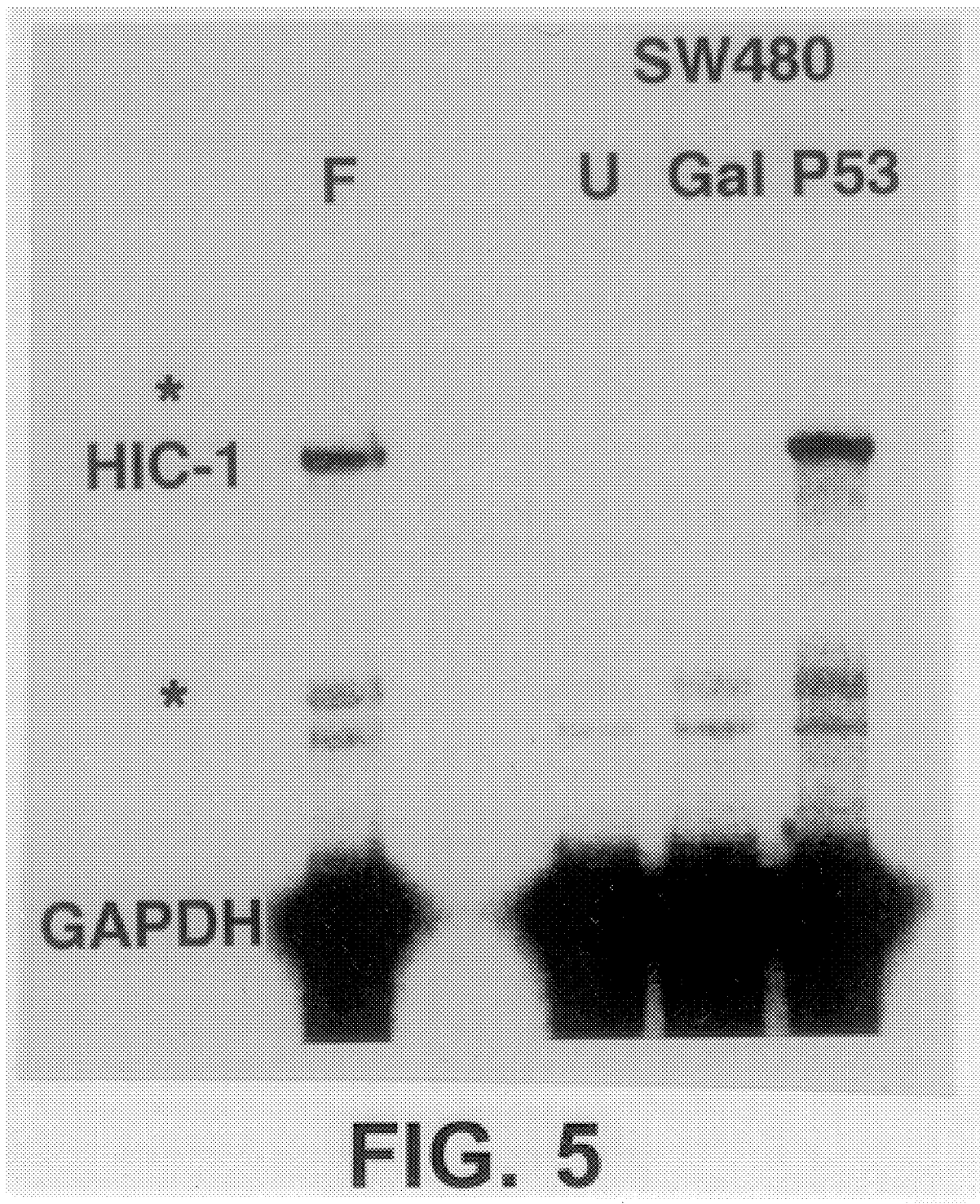
FIG. 5 shows an RNAse protection assay, as detailed in FIG. 4, after infection of an adenoviral vector containing either the β-galactosidase gene or the wild type human p53 gene into the SW480 line of human colon cancer cells. (Uninfected, normal, control human fibroblasts (F), uninfected SW480 cells (U), SW480 cells infected with the β-galactosidase gene (GAL), and SW480 cells infected with the p53 gene (p53)). Positions of the undigested HIC-1 and GAPDH probes and of the HIC-1 and GAPDH transcripts are marked exactly as in FIG. 4.

FIG. 5 shows an RNAse protection assay, as detailed in FIG. 4, after infection of an adenoviral vector containing either the β-galactosidase gene or the wild type human p53 gene into the SW480 line of human colon cancer cells. (Uninfected, normal, control human fibroblasts (F), uninfected SW480 cells (U), SW480 cells infected with the β-galactosidase gene (GAL), and SW480 cells infected with the p53 gene (p53)). Positions of the undigested HIC-1 and GAPDH probes and of the HIC-1 and GAPDH transcripts are marked exactly as in FIG. 4.

HIC-1 is expressed at only low levels in this cells line (FIG. 5A–U). When the wild type p53 gene is exogenously expressed in the SW480 cells, the level of HIC-1 expression is upregulated 20 fold (FIG. 5—p53), as compared to control cells (U & GAL). These results suggest that the tumor suppressor gene p53 activates HIC-1 expression, either directly or indirectly. However, since a p53 binding sites has been identified 4.0 kb upstream from the transcription start site (see enclosed map), it suggests a direct interaction between p53 and HIC-1. We are working to validate this type of interaction.

SUMMARY OF EXAMPLES

HIC-1 plays a significant role in normal and neoplastic cells. At least four other genes have thus far been identified as potential downstream targets of p53, including WAF1 (El-Deiry, W. S., et al., supra) MDM2 (Chen, C. Y., et al., Proc. Natl. Acad. Sci. USA, 91:2684–2688, 1994), GADD45 (Kastan, M. B., et al., Cell, 71:587–597, 1992) and BAX (Miyashita, T., et al., Oncogene, 9:1799–1805, 1994). HIC-1 probably functions as a transcription factor, as inferred by its structure and the characteristics of the other members of the Zin domain family. Two drosophila members, tram-track and broad complex, are transcriptional repressors which help regulate segmental development (Harrison and Travers, EMBO J 9:207, 1990; di Bello, et al., Genetics, 129:385, 1991). A third drosophila protein, GAGA appears to function by dynamically blocking the formation of nucleosomal structures which would impede transcriptional activation of promoter regions (Tsukiyama, T., et al., Nature, 367:525–532, 1994). The murine Zin domain gene, MZF5, has in-vitro transcriptional repressor activity for c-myc and thymidine kinase promoters (Numoto, et al., Nucleic Acids Res., 21:3767, 1993). Finally, two of the 4 other human Zin domain proteins were found as components of translocations in human neoplasms (Chardin, et al., Nucleic Acids Res., 19:1431, 1991; Hromas, et al., J. Biol. Chem., 266:14183, 1991; Chen, et al., EMBO J., 12:1161, 1993). Second, it is necessary to determine the precise interaction between p53 and the HIC-1 promoter.

In summary, the present invention identifies a new gene at 17p13.3, HIC-1, for which the expression pattern, structural motifs, chromosomal location, and p53 responsiveness are suggestive of an important function in tumorgenesis. Identification of the precise p53 pathway in which HIC-1 is involved should clarify the role of this gene in normal and neoplastic cells. Finally, the results suggest that in tumor DNA, identification of hypermethylated CpG islands associated with regions of allelic loss could facilitate the localization and cloning of candidate tumor suppressor genes as well as function as markers for recurrent abnormal growth or cells which may be resistant to particular therapeutic regimens.

The foregoing is meant to illustrate, but not to limit, the scope of the invention. Indeed, those of ordinary skill in the art can readily envision and produce further embodiments, based on the teachings herein, without undue experimentation.

We claim:

1. An isolated polynucleotide encoding a polypeptide having an amino acid sequence as set forth in SEQ ID NO: 3.

2. The isolated polynucleotide of claim 1 encoding a polypeptide having an amino acid sequence of SEQ ID NO: 3 and having at least one epitope for an antibody immunoreactive with hypermethylated in cancer-1 (HIC-1).

3. An isolated polynucleotide wherein the nucleotide sequence is selected from the group consisting of:

a) SEQ ID NO: 1, wherein T can also be U;

b) SEQ ID NO: 1; and c) nucleic acid sequences complementary to a) or b).

4. A recombinant expression vector which contains the polynucleotide of claim 1.

5. A host cell which contains the expression vector of claim 4.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 4616 base pairs
       (B) TYPE: nucleic acid
       (C) STRANDEDNESS: single
       (D) TOPOLOGY: linear (ii) MOLECULE TYPE: DNA (genomic)

(vii) IMMEDIATE SOURCE:
       (B) CLONE: HIC-1 polynucleotide (ix) FEATURE:
       (A) NAME/KEY: CDS
       (B) LOCATION: 1..4616

(xi) SEQUENCE DESCRIPTION: SEQ ID NO:1:

```
CCCGGCCCGC CGGGACCGCA GGTAACGGGC CGCGGGGCCC CGCGGGCCAG GAGGGGAACG      60

GGGTCGGGCG GCGAGCAGC GGGCAGGGGA GCTCAGGGCT CGGCTCCGGG CTCTGCCGCC      120

GGATTTGGGG GCCGCGAGGA AGAGCTGCGA GCCGAGGGCC TGGGGCCGGC GCACTCCTCC     180

CGCCCTGTCT GCAGTTGGAA AACTTTTCCC CAAGTTTGGG GCGGCGGAGT TCCGGGGGAG     240

AAGGGGCCGG GGGAGCCGCG GAGGGAGGCG CCGGGCCCGC GCGTGTAGGG CCCAGGCCGA     300

GGCCGGGACG CGGGTGGGGC GCAGGCCCGG GTCAGGGCCG CAGCCGGCTG TGCGCCGTGC     360

CCGCCCGGGG CGCTGCCCCC TCCCTCCCCT GGGAGCTGCG TGGCTCCCCC CTCCCCCCCA     420

CCTGCTTCCT GCCTCAGCCT CCTGCCCCGA TATAACGCCC TCCCCGCGCC GGGCCCGGCC     480

TTCGCGCTCT GCCCGCCACG GCAGCCGCTG CCTCCGCTCC CCGCGCGGCC GCCGCCCGGG     540

CCCCGACCGA GGGTTGACAG CCCCCGGCCA GGGCGGCGCC AGGGCGGGCA CCGCGCTCCC     600

CTCCTCCGTA TCACTTCCCC CAACTGGGGC AACTTCTCCC GAGGCGGGAG GCGCTGGTTC     660

CTCGGCTCCC TTTCTCCCTA CTTGGGTAAA GTTCTCCGCC CTGAATGACT TTTCCTGAAG     720

CGGACATTTT ACTTAAATCG GGTAACTGTC TCCAAAAGGG TCACTGCGCC TGAACAGTTT     780

TCTTCTCGGA AGCCCCAGCA CCCAGCCAGG TGCCCTGGGG CGTGCAGGCC GCCCTGGCCT     840

CCCCTCCACC GGCGGCCGCT CACCTCCTGC TCCTTCTCCT GGTCCGGGCG GGCCGGCCTG     900

GGCTCCCACT CCAGAGGGCA GCTGGTCCTT CGCCGGTGCC CAGGCCGCAG GGCTGATGCC     960

CCCGCTCAGC TGAGGGAAGG GGAAGTGGAG GGGAGAAGTG CCGGGCTGGG GCCAGGCGGC    1020

CAGGGCGCCG CACGGCTCTC ACCCGGCCGG TGTGTGTCCC CGCAGGAGAG TGTGCTGGGC    1080

AGACGATGCT GGACACGATG GAGGCGCCCG GCCACTCCAG GCAGCTGCTG CTGCAGCTCA    1140

ACAACCAGCG CACCAAGGGC TTCTTGTGCG ACGTGATCAT CGTGGTGCAG AACGCCCTCT    1200

TCCGCGCGCA CAAGAACGTG CTGGCGGCCA GCAGCGCCTA CCTCAAGTCC CTGGTGGTGC    1260

ATGACAACCT GCTCAACCTG GACCATGACA TGGTGAGCCC GGCCGTGTTC CGCCTGGTGC    1320

TGGACTTCAT CTACACCGGC CGCCTGGCTG ACGGCGCAGA GGCGGCTGCG GCCGCGGCCG    1380

TGGCCCCGGG GGCTGAGCCG AGCCTGGGCG CCGTGCTGGC CGCCGCCAGC TACCTGCAGA    1440

TCCCCGACCT CGTGGCGCTG TGCAAGAAAC GCCTCAAGCG CCACGGCAAG TACTGCCACC    1500

TGCGGGGCGG CGGCGGCGGC GGCGGCGGCT ACGCGCCCTA TGGTCGGCCG GGCCGGGGCC    1560

TGCGGGCCGC CACGCCGTCA TCCAGGCCTG CTACCCGTCC CCAGTCGGGC CTCCGCCGCC    1620
```

```
GCCTGCCGCG GAGCCGCCCT CGGGCCCAGA GGCCGCGGTC AACACGCACT GCGCCGAGCT    1680

GTACGCGTCG GGACCCGGCC CGGCCGCCGC ACTCTGTGCC TCGGAGCGCC GCTGCTCCCC    1740

TCTTTGTGGC CTGGACCTGT CCAAGAAGAG CCCGCCGGGC TCCGCGGCGC CAGAGCGGCC    1800

GCTGGCTGAG CGCGAGCTGC CCCCGCGCCC GGACAGCCCT CCCAGCGCCG GCCCCGCCGC    1860

CTACAAGGAG CCGCCTCTCG CCCTGCCGTC GCTGCCGCCG CTGCCCTTCC AGAAGCTGGA    1920

GGAGGCCGCA CCGCCTTCCG ACCCATTTCG CGGCGGCAGC GGCAGCCCGG ACCCGAGCC    1980

CCCCGGCCGC CCCAACGGGC CTAGTCTCCT CTATCGCTGG ATGAAGCACG AGCCGGGCCT    2040

GGGTAGCTAT GGCGACGAGC TGGGCCGGGA GCGCGGCTCC CCCAGCGAGC GCTGCGAAGA    2100

GCGTGGTGGG GACGCGGCCG TCTCGCCCGG GGGGCCCCCG CTCGGCCTGG CGCCGCCGCC    2160

GCGCTACCCT GGCAGCCTGG ACGGGCCCGG CGCGGGCGGC GACGGCGACG ACTACAAGAG    2220

CAGCAGCGAG GAGACCGGTA GCAGCGAGGA CCCCAGCACC GCCTGGCGGC CACCTCGAGG    2280

GCTACCCATG CCCGCACCTG GCCTATGGCG AGCCCGAGAG CTTCGGTGAC AACCTGTACG    2340

TGTGCATTCC GTGCGGCAAG GGCTTCCCCA GCTCTGAGCA GCTGAACGCG CACGTGGAGG    2400

CTCACGTGGA GGAGGAGGAA GCGCTGTACG GCAGGGCCGA GGCGGCCGAA GTGGCCGCTG    2460

GGGCCGCCGG CCTAGGGCCC CCTTTTGGAG GCGGCGGGA CAAGGTCGCC GGGGCTCCGG    2520

GTGGCCTGGG AGAGCTGCTG CGGCCCTACC GCTGCGGCTC GTGCGACAAG AGCTACAAGG    2580

ACCCGGCCAC GCTGCGGCAG CACGAGAAGA CGCACTGGCT GACCCGGCCC TACCCATGCA    2640

CCATCTGCGG GAAGAAGTTC ACGCAGCGTG GGACCATGAC GCGCCACATG CGCAGCCACC    2700

TGGGCCTCAA GCCCTTCGCG TGCGACGCGT GCGGCATGCG GTTCACGCGC CAGTACCGCC    2760

TCACCCGGAC GCACATGCGC ATCCACCCTC GCGGCGAGAA GCCCTACGAG TGCCAGGTGT    2820

GCGGCGGCAA GTTCGCACAG CAACGCAACC TCATCAGCCA CATGAAGATG CACGCCGTGG    2880

GGGGCGCGGC GGCGCGGCCG GGGCGCTGGC GGGCTTGGGG GGGCTCCCCG GCGTCCCCGG    2940

CCCCGACGGC AAGGGCAAGC TCGACTTCCC CGAGGGCGTC TTTGCTGTGG CTCGCTCACG    3000

GCCGAGCAGC TGAGCCTGAA GCAGCAGGAC AAGGCGGCCG CGACCGAGCT GCTGGCGCAG    3060

ACCACGCACT TCCTGCACGA CCCCAAGGTG GCGCTGGAGA GCCTCTACCC GCTGGCCAAG    3120

TTCACGGCCG AGCTGGGCCT CAGCCCCGAC AAGGCGGCCG AGGTGCTGAG CCAGGGCGCT    3180

CACCTGGCGG CCGGGCCCGA CGGCGGACCA TCGACCGTTT CTCTCCCACC TAGAGCGCCC    3240

CTCGCCAGCC CGCTCTGTCG CTGCTGCGCG GCCCTGGCCC GCACCCCAGG GAGCGGCGGG    3300

GGCGGCGCGC AGGGCCCACT GTGCCCGGGA CAACCGCAGC GTCGCCACAG TGGCGGCTCC    3360

ACCTCTCGGC GGCCTCACCT GGCCTCACTG CTTCGTGCCT TAGCTCGGGG GTCGGGGGAG    3420

AACCCCGGGA CGGGGTGGGA TGGGGTAAGG GAAATTTATA TTTTTGATAT CAGCTTTGAC    3480

CAAAGGAGAC CCCAGGCCCC TCCCGCCTCT TCCTGTGGTT CGTCGGCCCC CTCCCCCGGC    3540

TCCGCGCTGC TCTTAGAGGG GGAGGGGTGT CACTGTCGGG GCACTCCTAG CCCTACCTCC    3600

GGCCCTTGCG ACCACACCCA TTCTCACTGT GAATCTCCCC GCTGGGTCGG AGCGTCGGGC    3660

AGAGTTGGGG AGTGGGAGG GGACTGAGCC GGCCGGAGGC CCCCGCACCC CCGCTCCCAC    3720

CCACCCCGGG ACTGATAATG TGAAGTTCCT CATTTTGCAC AAGTGGCACT AGCCCAGGGC    3780

CAACCCTTCC TTCCTCAGTC ACCAAGGGCG GGGAGTTCTG GAGTCGGAAG GCGAAGAGCC    3840

TACCACCAGG TCTCCCACTC CCGCGGTGCC CTCCCTTCCC TTCCCTGCGG CCCCGGACCA    3900

TATTTATTGC ATGCGCCCCG GCGGCCCCCC ATCCCGAGCC CAGGCTGGGC TGGGCTGGAA    3960

CGCGGTCTCT TTAGCTCCCT CCTCTTCGTT TGTATATTTC CTACCTTGTA CACAGCTCTT    4020
```

```
CCAGAGCCGC TTCCATTTTC TATACTCGAA CCAAACAGCA ATAAAGCAGT AACCAAGGAC      4080

CCCGACCCCG CTGCTCTCTT CTGCCCCTGC ACAAGGACCT GGATGCTGCG CCCGCTGGGT      4140

GGAGGAGCCA GAAAGGGCCA CCCTCACACA GGTGCAGAGG CTTGGACCTG CCTCCCTCCC      4200

CAGTCCCAGA AACAGATCAG CAAGAGGTCA GGTATGTTTC ATAACTAAAA ATTTATTAAG      4260

GAAACAAAAC CAGTGCTGCA AACGGGACAG AAAGGAGAGC TGGGTCTCCC TCCCGACCAC      4320

CCAGTCATCG GCCTTCCAGC TGGGGAGAGA ATCTTAAAGG AGAGGCCGGG GACCCTGTAC      4380

TCCAAAGAGC CCAGTCTTCT GAGACTCTAG GGGACTCCTA CCCCCAAACT ACTGGCCTTG      4440

GCTCCCCTAC ACGGTACCCC ATCGCTTCTG GCATAGTCCT GGGCCTCAGG GAGGGCAGAG      4500

CTGCGCACCC ATCCTCCAGG CAGGCTGTGC AGTCAGGCCA TGGGCTCTGG GGTATCCCCC      4560

ACTGGTCCCA TTAAGATTTG CCCCTGGCTC CACCGAAAAC CCCGTCTTCC CCTAAG         4616

(2) INFORMATION FOR SEQ ID NO:2:

(i) SEQUENCE CHARACTERISTICS:
        (A) LENGTH: 4112 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: HIC-1 coding polynucleotide (ix) FEATURE:
        (A) NAME/KEY: CDS
        (B) LOCATION: 1086..2726

(xi) SEQUENCE DESCRIPTION: SEQ ID NO:2:

CCCGGCCCGC CGGGACCGCA GGTAACGGGC CGCGGGGCCC CGCGGGCCAG GAGGGGAACG        60

GGGTCGGGCG GGCGAGCAGC GGGCAGGGGA GCTCAGGGCT CGGCTCCGGG CTCTGCCGCC       120

GGATTTGGGG GCCGCGAGGA AGAGCTGCGA GCCGAGGGCC TGGGGCCGGC GCACTCCTCC       180

CGCCCTGTCT GCAGTTGGAA AACTTTTCCC CAAGTTTGGG GCGGCGGAGT TCCGGGGGAG       240

AAGGGGCCGG GGGAGCCGCG GAGGGAGGCG CCGGGCCCGC GCGTGTAGGG CCCAGGCCGA       300

GGCCGGGACG CGGGTGGGGC GCAGGCCCGG GTCAGGGCCC CAGCCGGCTG TGCGCCGTGC       360

CCGCCCGGGG CGCTGCCCCC TCCCTCCCCT GGGAGCTGCG TGGCTCCCCC CTCCCCCCCA       420

CCTGCTTCCT GCCTCAGCCT CCTGCCCCGA TATAACGCCC TCCCCGCGCC GGGCCCGGCC       480

TTCGCGCTCT GCCCGCCACG GCAGCCGCTG CCTCCGCTCC CCGCGCGGCC GCCGCCCGGG       540

CCCCGACCGA GGGTTGACAG CCCCCGGCCA GGGCGGCGCC AGGGCGGGCA CCGCGCTCCC       600

CTCCTCCGTA TCACTTCCCC CAACTGGGGC AACTTCTCCC GAGGCGGGAG GCGCTGGTTC       660

CTCGGCTCCC TTTCTCCCTA CTTGGGTAAA GTTCTCCGCC CTGAATGACT TTTCCTGAAG       720

CGGACATTTT ACTTAAATCG GGTAACTGTC TCCAAAAGGG TCACTGCGCC TGAACAGTTT       780

TCTTCTCGGA AGCCCCAGCA CCCAGCCAGG TGCCCTGGGG CGTGCAGGCC GCCCTGGCCT       840

CCCCTCCACC GGCGGCCGCT CACCTCCTGC TCCTTCTCCT GGTCCGGGCG GGCCGGCCTG       900

GGCTCCCACT CCAGAGGGCA GCTGGTCCTT CGCCGGTGCC CAGGCCGCAG GGCTGATGCC       960

CCCGCTCAGC TGAGGGAAGG GGAAGTGGAG GGGAGAAGTG CCGGGCTGGG GCCAGGCGGC      1020

CAGGGCGCCG CACGGCTCTC ACCCGGCCGG TGTGTGTCCC CGCAGGAGAG TGTGCTGGGC      1080

AGACG ATG CTG GAC ACG ATG GAG GCG CCC GGC CAC TCC AGG CAG CTG         1127
      Met Leu Asp Thr Met Glu Ala Pro Gly His Ser Arg Gln Leu
      1               5                  10
```

-continued

| | |
|---|---|
| CTG CTG CAG CTC AAC AAC CAG CGC ACC AAG GGC TTC TTG TGC GAC GTG<br>Leu Leu Gln Leu Asn Asn Gln Arg Thr Lys Gly Phe Leu Cys Asp Val<br>15                    20                    25                    30 | 1175 |
| ATC ATC GTG GTG CAG AAC GCC CTC TTC CGC GCG CAC AAG AAC GTG CTG<br>Ile Ile Val Val Gln Asn Ala Leu Phe Arg Ala His Lys Asn Val Leu<br>35                    40                    45 | 1223 |
| GCG GCC AGC AGC GCC TAC CTC AAG TCC CTG GTG GTG CAT GAC AAC CTG<br>Ala Ala Ser Ser Ala Tyr Leu Lys Ser Leu Val Val His Asp Asn Leu<br>50                    55                    60 | 1271 |
| CTC AAC CTG GAC CAT GAC ATG GTG AGC CCG GCC GTG TTC CGC CTG GTG<br>Leu Asn Leu Asp His Asp Met Val Ser Pro Ala Val Phe Arg Leu Val<br>65                    70                    75 | 1319 |
| CTG GAC TTC ATC TAC ACC GGC CGC CTG GCT GAC GGC GCA GAG GCG GCT<br>Leu Asp Phe Ile Tyr Thr Gly Arg Leu Ala Asp Gly Ala Glu Ala Ala<br>80                    85                    90 | 1367 |
| GCG GCC GCG GCC GTG GCC CCG GGG GCT GAG CCG AGC CTG GGC GCC GTG<br>Ala Ala Ala Ala Val Ala Pro Gly Ala Glu Pro Ser Leu Gly Ala Val<br>95                    100                105            110 | 1415 |
| CTG GCC GCC GCC AGC TAC CTG CAG ATC CCC GAC CTC GTG GCG CTG TGC<br>Leu Ala Ala Ala Ser Tyr Leu Gln Ile Pro Asp Leu Val Ala Leu Cys<br>115                  120                125 | 1463 |
| AAG AAA CGC CTC AAG CGC CAC GGC AAG TAC TGC CAC CTG CGG GGC GGC<br>Lys Lys Arg Leu Lys Arg His Gly Lys Tyr Cys His Leu Arg Gly Gly<br>130                  135                140 | 1511 |
| GGC GGC GGC GGC GGC GGC TAC GCG CCC TAT GCT ATG GCG ACG AGC TGG<br>Gly Gly Gly Gly Gly Gly Tyr Ala Pro Tyr Ala Met Ala Thr Ser Trp<br>145                  150                155 | 1559 |
| GCC GGG AGC GCG GCT CCC CCA GCG AGC GCT GCG AAG AGC GTG GTG GGG<br>Ala Gly Ser Ala Ala Pro Pro Ala Ser Ala Ala Lys Ser Val Val Gly<br>160                  165                170 | 1607 |
| ACG CGG CCG TCT CGC CCG GGG GGC CCC CGC TCG GCC TGG CGC CGC CGC<br>Thr Arg Pro Ser Arg Pro Gly Gly Pro Arg Ser Ala Trp Arg Arg Arg<br>175                  180                185            190 | 1655 |
| CGC GCT ACC CTG GCA GCC TGG ACG GGC CCG GCG CGG GCG GCG ACG GCG<br>Arg Ala Thr Leu Ala Ala Trp Thr Gly Pro Ala Arg Ala Ala Thr Ala<br>195                  200                205 | 1703 |
| ACG ACT ACA AGA GCA GCA GCG AGG AGA CCG GTA GCA GCG AGG ACC CCA<br>Thr Thr Thr Arg Ala Ala Ala Arg Arg Pro Val Ala Ala Arg Thr Pro<br>210                  215                220 | 1751 |
| GCA CCG CCT GGC GGC CAC CTC GAG GGC TAC CCA TGC CCG CAC CTG GCC<br>Ala Pro Pro Gly Gly His Leu Glu Gly Tyr Pro Cys Pro His Leu Ala<br>225                  230                235 | 1799 |
| TAT GGC GAG CCC GAG AGC TTC GGT GAC AAC CTG TAC GTG TGC ATT CCG<br>Tyr Gly Glu Pro Glu Ser Phe Gly Asp Asn Leu Tyr Val Cys Ile Pro<br>240                  245                250 | 1847 |
| TGC GGC AAG GGC TTC CCC AGC TCT GAG CAG CTG AAC GCG CAC GTG GAG<br>Cys Gly Lys Gly Phe Pro Ser Ser Glu Gln Leu Asn Ala His Val Glu<br>255                  260                265            270 | 1895 |
| GCT CAC GTG GAG GAG GAG GAA GCG CTG TAC GGC AGG GCC GAG GCG GCC<br>Ala His Val Glu Glu Glu Glu Ala Leu Tyr Gly Arg Ala Glu Ala Ala<br>275                  280                285 | 1943 |
| GAA GTG GCC GCT GGG GCC GCC GGC CTA GGG CCC CCT TTT GGA GGC GGC<br>Glu Val Ala Ala Gly Ala Ala Gly Leu Gly Pro Pro Phe Gly Gly Gly<br>290                  295                300 | 1991 |
| GGG GAC AAG GTC GCC GGG GCT CCG GGT GGC CTG GGA GAG CTG CTG CGG<br>Gly Asp Lys Val Ala Gly Ala Pro Gly Gly Leu Gly Glu Leu Leu Arg<br>305                  310                315 | 2039 |
| CCC TAC CGC TGC GGC TCG TGC GAC AAG AGC TAC AAG GAC CCG GCC ACG<br>Pro Tyr Arg Cys Gly Ser Cys Asp Lys Ser Tyr Lys Asp Pro Ala Thr<br>320                  325                330 | 2087 |

```
CTG CGG CAG CAC GAG AAG ACG CAC TGG CTG ACC CGG CCC TAC CCA TGC     2135
Leu Arg Gln His Glu Lys Thr His Trp Leu Thr Arg Pro Tyr Pro Cys
335                 340                 345                 350

ACC ATC TGC GGG AAG AAG TTC ACG CAG CGT GGG ACC ATG ACG CGC CAC     2183
Thr Ile Cys Gly Lys Lys Phe Thr Gln Arg Gly Thr Met Thr Arg His
                355                 360                 365

ATG CGC AGC CAC CTG GGC CTC AAG CCC TTC GCG TGC GAC GCG TGC GGC     2231
Met Arg Ser His Leu Gly Leu Lys Pro Phe Ala Cys Asp Ala Cys Gly
            370                 375                 380

ATG CGG TTC ACG CGC CAG TAC CGC CTC ACC CGG ACG CAC ATG CGC ATC     2279
Met Arg Phe Thr Arg Gln Tyr Arg Leu Thr Arg Thr His Met Arg Ile
        385                 390                 395

CAC CCT CGC GGC GAG AAG CCC TAC GAG TGC CAG GTG TGC GGC GGC AAG     2327
His Pro Arg Gly Glu Lys Pro Tyr Glu Cys Gln Val Cys Gly Gly Lys
    400                 405                 410

TTC GCA CAG CAA CGC AAC CTC ATC AGC CAC ATG AAG ATG CAC GCC GTG     2375
Phe Ala Gln Gln Arg Asn Leu Ile Ser His Met Lys Met His Ala Val
415                 420                 425                 430

GGG GGC GCG GCG GCG CGG CCG GGG CGC TGG CGG GCT TGG GGG GGC TCC     2423
Gly Gly Ala Ala Ala Arg Pro Gly Arg Trp Arg Ala Trp Gly Gly Ser
                435                 440                 445

CCG GCG TCC CCG GCC CCG ACG GCA AGG GCA AGC TCG ACT TCC CCG AGG     2471
Pro Ala Ser Pro Ala Pro Thr Ala Arg Ala Ser Ser Thr Ser Pro Arg
            450                 455                 460

GCG TCT TTG CTG TGG CTC GCT CAC GGC CGA GCA GCT GAG CCT GAA GCA     2519
Ala Ser Leu Leu Trp Leu Ala His Gly Arg Ala Ala Glu Pro Glu Ala
        465                 470                 475

GCA GGA CAA GGC GGC CGC GAC CGA GCT GCT GGC GCA GAC CAC GCA CTT     2567
Ala Gly Gln Gly Gly Arg Asp Arg Ala Ala Gly Ala Asp His Ala Leu
    480                 485                 490

CCT GCA CGA CCC CAA GGT GGC GCT GGA GAG CCT CTA CCC GCT GGC CAA     2615
Pro Ala Arg Pro Gln Gly Gly Ala Gly Glu Pro Leu Pro Ala Gly Gln
495                 500                 505                 510

GTT CAC GGC CGA GCT GGG CCT CAG CCC CGA CAA GGC GGC CGA GGT GCT     2663
Val His Gly Arg Ala Gly Pro Gln Pro Arg Gln Gly Gly Arg Gly Ala
                515                 520                 525

GAG CCA GGG CGC TCA CCT GGC GGC CGG GCC CGA CGG CGG ACC ATC GAC     2711
Glu Pro Gly Arg Ser Pro Gly Gly Arg Ala Arg Arg Arg Thr Ile Asp
            530                 535                 540

CGT TTC TCT CCC ACC TAGAGCGCCC CTCGCCAGCC CGCTCTGTCG CTGCTGCGCG    2766
Arg Phe Ser Pro Thr
            545

GCCCTGGCCC GCACCCCAGG GAGCGGCGGG GGCGGCGCGC AGGGCCCACT GTGCCCGGGA    2826

CAACCGCAGC GTCGCCACAG TGGCGGCTCC ACCTCTCGGC GGCCTCACCT GGCCTCACTG    2886

CTTCGTGCCT TAGCTCGGGG GTCGGGGGAG AACCCCGGGA CGGGGTGGGA TGGGGTAAGG    2946

GAAATTTATA TTTTTGATAT CAGCTTTGAC CAAAGGAGAC CCCAGGCCCC TCCCGCCTCT    3006

TCCTGTGGTT CGTCGGCCCC CTCCCCCGGC TCCGCGCTGC TCTTAGAGGG GGAGGGGTGT    3066

CACTGTCGGG GCACTCCTAG CCCTACCTCC GGCCCTTGCG ACCACACCCA TTCTCACTGT    3126

GAATCTCCCC GCTGGGTCGG AGCGTCGGGC AGAGTTGGGG AGTGGGGAGG GGACTGAGCC    3186

GGCCGGAGGC CCCCGCACCC CCGCTCCCAC CCACCCCGGG ACTGATAATG TGAAGTTCCT    3246

CATTTTGCAC AAGTGGCACT AGCCCAGGGC CAACCCTTCC TTCCTCAGTC ACCAAGGGCG    3306

GGGAGTTCTG GAGTCGGAAG GCGAAGAGCC TACCACCAGG TCTCCCACTC CCGCGGTGCC    3366

CTCCCTTCCC TTCCCTGCGG CCCCGGACCA TATTTATTGC ATGCGCCCCG GCGGCCCCCC    3426

ATCCCGAGCC CAGGCTGGGC TGGGCTGGAA CGCGGTCTCT TTAGCTCCCT CCTCTTCGTT    3486
```

-continued

```
TGTATATTTC CTACCTTGTA CACAGCTCTT CCAGAGCCGC TTCCATTTTC TATACTCGAA     3546

CCAAACAGCA ATAAAGCAGT AACCAAGGAC CCCGACCCCG CTGCTCTCTT CTGCCCCTGC     3606

ACAAGGACCT GGATGCTGCG CCCGCTGGGT GGAGGAGCCA GAAAGGGCCA CCCTCACACA     3666

GGTGCAGAGG CTTGGACCTG CCTCCCTCCC CAGTCCCAGA AACAGATCAG CAAGAGGTCA     3726

GGTATGTTTC ATAACTAAAA ATTTATTAAG GAAACAAAAC CAGTGCTGCA AACGGGACAG     3786

AAAGGAGAGC TGGGTCTCCC TCCCGACCAC CCAGTCATCG GCCTTCCAGC TGGGGAGAGA     3846

ATCTTAAAGG AGAGGCCGGG GACCCTGTAC TCCAAAGAGC CCAGTCTTCT GAGACTCTAG     3906

GGGACTCCTA CCCCCAAACT ACTGGCCTTG GCTCCCCTAC ACGGTACCCC ATCGCTTCTG     3966

GCATAGTCCT GGGCCTCAGG GAGGGCAGAG CTGCGCACCC ATCCTCCAGG CAGGCTGTGC     4026

AGTCAGGCCA TGGGCTCTGG GGTATCCCCC ACTGGTCCCA TTAAGATTTG CCCCTGGCTC     4086

CACCGAAAAC CCCGTCTTCC CCTAAG                                         4112
```

(2) INFORMATION FOR SEQ ID NO:3:

(i) SEQUENCE CHARACTERISTICS:
        (A) LENGTH: 547 amino acids
        (B) TYPE: amino acid
        (D) TOPOLOGY: linear (ii) MOLECULE TYPE: protein (xi) SEQUENCE DESCRIPTION: SEQ ID NO:3:

```
Met Leu Asp Thr Met Glu Ala Pro Gly His Ser Arg Gln Leu Leu Leu
 1               5                  10                  15

Gln Leu Asn Asn Gln Arg Thr Lys Gly Phe Leu Cys Asp Val Ile Ile
                20                  25                  30

Val Val Gln Asn Ala Leu Phe Arg Ala His Lys Asn Val Leu Ala Ala
            35                  40                  45

Ser Ser Ala Tyr Leu Lys Ser Leu Val Val His Asp Asn Leu Leu Asn
        50                  55                  60

Leu Asp His Asp Met Val Ser Pro Ala Val Phe Arg Leu Val Leu Asp
 65                  70                  75                  80

Phe Ile Tyr Thr Gly Arg Leu Ala Asp Gly Ala Glu Ala Ala Ala
                85                  90                  95

Ala Ala Val Ala Pro Gly Ala Glu Pro Ser Leu Gly Ala Val Leu Ala
               100                 105                 110

Ala Ala Ser Tyr Leu Gln Ile Pro Asp Leu Val Ala Leu Cys Lys Lys
           115                 120                 125

Arg Leu Lys Arg His Gly Lys Tyr Cys His Leu Arg Gly Gly Gly
       130                 135                 140

Gly Gly Gly Gly Tyr Ala Pro Tyr Ala Met Ala Thr Ser Trp Ala Gly
145                 150                 155                 160

Ser Ala Ala Pro Pro Ala Ser Ala Ala Lys Ser Val Val Gly Thr Arg
               165                 170                 175

Pro Ser Arg Pro Gly Pro Arg Ser Ala Trp Arg Arg Arg Ala
           180                 185                 190

Thr Leu Ala Ala Trp Thr Gly Pro Ala Arg Ala Ala Thr Ala Thr Thr
       195                 200                 205

Thr Arg Ala Ala Ala Arg Arg Pro Val Ala Ala Arg Thr Pro Ala Pro
   210                 215                 220

Pro Gly Gly His Leu Glu Gly Tyr Pro Cys Pro His Leu Ala Tyr Gly
225                 230                 235                 240
```

```
Glu Pro Glu Ser Phe Gly Asp Asn Leu Tyr Val Cys Ile Pro Cys Gly
                245                 250                 255

Lys Gly Phe Pro Ser Glu Gln Leu Asn Ala His Val Glu Ala His
        260                 265                 270

Val Glu Glu Glu Ala Leu Tyr Gly Arg Ala Glu Ala Ala Glu Val
        275                 280                 285

Ala Ala Gly Ala Ala Gly Leu Gly Pro Pro Phe Gly Gly Gly Asp
        290                 295                 300

Lys Val Ala Gly Ala Pro Gly Gly Leu Gly Glu Leu Leu Arg Pro Tyr
305                 310                 315                 320

Arg Cys Gly Ser Cys Asp Lys Ser Tyr Lys Asp Pro Ala Thr Leu Arg
                325                 330                 335

Gln His Glu Lys Thr His Trp Leu Thr Arg Pro Tyr Pro Cys Thr Ile
                340                 345                 350

Cys Gly Lys Lys Phe Thr Gln Arg Gly Thr Met Thr Arg His Met Arg
                355                 360                 365

Ser His Leu Gly Leu Lys Pro Phe Ala Cys Asp Ala Cys Gly Met Arg
    370                 375                 380

Phe Thr Arg Gln Tyr Arg Leu Thr Arg His Met Arg Ile His Pro
385                 390                 395                 400

Arg Gly Glu Lys Pro Tyr Glu Cys Gln Val Cys Gly Lys Phe Ala
                405                 410                 415

Gln Gln Arg Asn Leu Ile Ser His Met Lys Met His Ala Val Gly Gly
                420                 425                 430

Ala Ala Ala Arg Pro Gly Arg Trp Arg Ala Trp Gly Ser Pro Ala
                435                 440                 445

Ser Pro Ala Pro Thr Ala Arg Ala Ser Ser Thr Ser Pro Arg Ala Ser
    450                 455                 460

Leu Leu Trp Leu Ala His Gly Arg Ala Ala Glu Pro Glu Ala Ala Gly
465                 470                 475                 480

Gln Gly Gly Arg Asp Arg Ala Ala Gly Ala Asp His Ala Leu Pro Ala
                485                 490                 495

Arg Pro Gln Gly Gly Ala Gly Glu Pro Leu Pro Ala Gly Gln Val His
                500                 505                 510

Gly Arg Ala Gly Pro Gln Pro Arg Gln Gly Arg Gly Ala Glu Pro
                515                 520                 525

Gly Arg Ser Pro Gly Gly Arg Ala Arg Arg Thr Ile Asp Arg Phe
530                 535                 540

Ser Pro Thr
545

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GGTCTTGTGC AGAGGCATGG TC                                           22

(2) INFORMATION FOR SEQ ID NO:5:

(i) SEQUENCE CHARACTERISTICS:
        (A) LENGTH: 104 amino acids
```

(B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

Gly Asp Tyr Gly Thr Ser Leu Val Ser Ala Ile Gln Leu Leu Arg Cys
1               5                   10                  15

His Gly Asp Leu Val Asp Cys Thr Leu Ala Ala Gly Gly Arg Ser Phe
            20                  25                  30

Pro Ala His Lys Ile Val Leu Cys Ala Ala Ser Pro Phe Leu Leu Asp
            35                  40                  45

Leu Leu Lys Asn Thr Pro Cys Lys His Pro Val Met Leu Ala Gly
        50                  55                  60

Val Asn Ala Asn Asp Leu Glu Ala Leu Leu Glu Phe Val Tyr Arg Gly
65                  70                  75                  80

Glu Val Ser Val Asp His Ala Gln Leu Pro Ser Leu Leu Gln Ala Ala
                85                  90                  95

Gln Cys Leu Asn Ile Gln Gly Leu
            100

(2) INFORMATION FOR SEQ ID NO:6:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Asn Asn His Gln Ser Asn Leu Leu Ser Val Phe Asp Gln Leu Leu His
1               5                   10                  15

Ala Glu Thr Phe Val Asp Val Thr Leu Ala Val Glu Gly Gln His Leu
            20                  25                  30

Lys Ala His Lys Met Val Leu Ser Ala Cys Ser Pro Tyr Phe Asn Thr
            35                  40                  45

Leu Phe Val Ser His Pro Glu Lys His Pro Ile Val Ile Leu Lys Asp
        50                  55                  60

Val Pro Tyr Ser Asp Met Lys Ser Leu Leu Asp Phe Met Tyr Arg Gly
65                  70                  75                  80

Glu Val Ser Val Asp Gln Glu Arg Leu Thr Ala Phe Leu Arg Val Ala
                85                  90                  95

Glu Ser Leu Arg Ile Lys Gly Leu
            100

(2) INFORMATION FOR SEQ ID NO:7:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

Asn Asn Tyr Gln Ser Ser Ile Thr Ser Ala Phe Glu Asn Leu Arg Asp
1               5                   10                  15

Asp Glu Ala Phe Val Asp Val Thr Leu Ala Cys Glu Gly Arg Ser Ile

-continued

```
                    20                  25                  30
Lys Ala His Arg Val Val Leu Ser Ala Cys Ser Pro Tyr Phe Arg Glu
                35                  40                  45
Leu Leu Lys Ser Thr Pro Cys Lys His Pro Val Ile Leu Leu Gln Asp
 50                  55                  60
Val Asn Phe Met Asp Leu His Ala Leu Val Glu Phe Ile Tyr His Gly
 65                  70                  75                  80
Glu Val Asn Val His Gln Lys Ser Leu Gln Ser Phe Leu Lys Thr Ala
                85                  90                  95
Glu Val Leu Arg Val Ser Gly Leu
                100
```

(2) INFORMATION FOR SEQ ID NO:8:

(i) SEQUENCE CHARACTERISTICS:
        (A) LENGTH: 105 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

```
Asp Asp His Lys Thr Leu Phe Leu Lys Thr Leu Asn Glu Gln Arg Leu
 1               5                  10                  15
Glu Gly Glu Phe Cys Asp Ile Ala Ile Val Val Glu Asp Val Lys Phe
                20                  25                  30
Arg Ala His Arg Cys Val Leu Ala Ala Cys Ser Thr Tyr Phe Lys Lys
                35                  40                  45
Leu Phe Lys Lys Leu Glu Val Asp Ser Ser Val Ile Glu Ile Asp
 50                  55                  60
Phe Leu Arg Ser Asp Ile Phe Glu Glu Val Leu Asn Tyr Met Tyr Thr
 65                  70                  75                  80
Ala Lys Ile Ser Val Lys Lys Glu Asp Val Asn Leu Met Met Ser Ser
                85                  90                  95
Gly Gln Ile Leu Gly Ile Arg Phe Leu
                100                 105
```

(2) INFORMATION FOR SEQ ID NO:9:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Ala Ser His Ser Leu Val Leu Leu Gln Gln Leu Asn Met Gln Arg Glu
 1               5                  10                  15
Phe Gly Phe Leu Cys Asp Cys Thr Val Ala Ile Gly Asp Val Tyr Phe
                20                  25                  30
Lys Ala His Arg Ala Val Leu Ala Ala Phe Ser Asn Tyr Phe Lys Met
                35                  40                  45
Ile Phe Ile His Gln Thr Ser Glu Cys Ile Lys Ile Gln Pro Thr Asp
 50                  55                  60
Ile Gln Pro Asp Ile Phe Ser Tyr Leu Leu His Ile Met Tyr Thr Gly
 65                  70                  75                  80
Lys Gly Pro Lys Gln Ile Val Asp His Ser Arg Leu Glu Glu Gly Ile
```

```
                     85                  90                  95
Arg Phe Leu His Ala Asp Tyr Leu
                100

(2) INFORMATION FOR SEQ ID NO:10:

(i) SEQUENCE CHARACTERISTICS:
        (A) LENGTH: 106 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

Thr Arg His Ala Ser Asp Val Leu Leu Asn Leu Asn Arg Leu Arg Ser
1               5                  10                  15

Arg Asp Ile Leu Thr Asp Val Val Ile Val Val Ser Arg Glu Gln Phe
             20                  25                  30

Arg Ala His Lys Thr Val Leu Met Ala Cys Ser Gly Leu Phe Tyr Ser
             35                  40                  45

Ile Phe Thr Asp Gln Leu Lys Cys Asn Leu Ser Val Ile Asn Leu Asp
50                  55                  60

Pro Glu Ile Asn Pro Glu Gly Phe Cys Ile Leu Leu Asp Phe Met Tyr
65                  70                  75                  80

Thr Ser Arg Leu Asn Leu Arg Glu Gly Asn Ile Met Ala Val Met Ala
                85                  90                  95

Thr Ala Met Tyr Leu Gln Met Glu His Val
                100                 105

(2) INFORMATION FOR SEQ ID NO:11:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Pro Ser His Pro Thr Gly Leu Leu Cys Lys Ala Asn Gln Met Arg Leu
1               5                  10                  15

Ala Gly Thr Leu Cys Asp Val Val Ile Met Val Asp Ser Gln Glu Phe
             20                  25                  30

His Ala His Arg Thr Val Leu Ala Cys Thr Ser Met Phe Glu Ile Leu
             35                  40                  45

Phe Arg His Arg Asn Ser Gln His Tyr Thr Leu Asp Phe Leu Ser Pro
50                  55                  60

Lys Thr Phe Gln Gln Ile Leu Gly Tyr Ala Tyr Thr Ala Thr Leu Gln
65                  70                  75                  80

Ala Lys Ala Glu Asp Leu Asp Asp Leu Leu Tyr Ala Ala Glu Ile Leu
                85                  90                  95

Glu Ile Glu Tyr Leu
                100

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: Not Relevant
```

(D) TOPOLOGY: linear (ii) MOLECULE TYPE: protein (xi) SEQUENCE DESCRIPTION: SEQ ID NO:12:

```
Val Gln His Ser Val Arg Val Leu Gln Glu Leu Asn Lys Gln Arg Glu
1               5                   10                  15

Lys Gly Gln Tyr Cys Asp Ala Thr Leu Asp Val Gly Gly Leu Val Phe
                20                  25                  30

Lys Ala His Trp Ser Val Leu Ala Cys Cys Ser His Phe Phe Gln Ser
                35                  40                  45

Leu Tyr Gly Asp Gly Ser Gly Gly Ser Val Val Leu Pro Ala Gly Phe
                50                  55                  60

Ala Glu Ile Phe Gly Leu Leu Leu Asp Phe Phe Tyr Thr Gly His Leu
65                  70                  75                  80

Ala Leu Thr Ser Gly Asn Arg Asp Gln Val Leu Leu Ala Ala Arg Glu
                85                  90                  95

Leu Arg Val Pro Glu Ala
                100
```

(2) INFORMATION FOR SEQ ID NO:13:

(i) SEQUENCE CHARACTERISTICS:
        (A) LENGTH: 101 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

```
Pro Gly His Ser Arg Gln Leu Leu Gln Leu Asn Asn Gln Arg Thr
1               5                   10                  15

Lys Gly Phe Leu Cys Asp Val Ile Ile Val Gln Asn Ala Leu Phe
                20                  25                  30

Arg Ala His Lys Asn Val Leu Ala Ala Ser Ser Ala Tyr Leu Lys Ser
                35                  40                  45

Leu Val Val His Asp Asn Leu Leu Asn Leu Asp His Asp Met Val Ser
                50                  55                  60

Pro Ala Val Phe Arg Leu Val Leu Asp Phe Ile Tyr Thr Gly Arg Leu
65                  70                  75                  80

Ala Ala Glu Pro Ser Leu Gly Ala Val Leu Ala Ala Ser Tyr Leu
                85                  90                  95

Gln Ile Pro Asp Leu
                100
```

(2) INFORMATION FOR SEQ ID NO:14:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

```
Asp Gly Ala Glu Ala Ala Ala Ala Ala Val Ala Pro Gly
1               5                   10
```